United States Patent [19]
Arnold

[11] Patent Number: 6,110,700
[45] Date of Patent: Aug. 29, 2000

[54] PRAD1 CYCLIN AND ITS CDNA

[75] Inventor: Andrew Arnold, Newton, Mass.

[73] Assignee: The General Hospital Corporation, Boston, Mass.

[21] Appl. No.: 07/667,711

[22] Filed: Mar. 11, 1991

[51] Int. Cl.$^7$ .................................................. C12N 15/12
[52] U.S. Cl. ........................ 435/69.1; 536/23.5; 435/6; 435/320.1; 435/325
[58] Field of Search ................... 536/27, 23.5; 435/69.1, 435/240.2, 252.3, 252.33, 320.1, 6, 325

[56] References Cited

U.S. PATENT DOCUMENTS 5,118,615  6/1992  Matsuo ..................................... 435/69.1

OTHER PUBLICATIONS

Raffield, M. et al., *Blood*, 78(2):259–63, Jul. 1991.
Sambrook et al., *Molecular Cloning : A Laboratory Manual*, 2nd Ed., Cold Spring Harbor Laboratory, 1989, pp. 18.76 and 18.81.
Hunt, Nature 350:462–463, 1991.
Lew et al., Cell 66:1197–1206, 1991.
Matsushime et al., Cell 65:701–713, 1991.
Motokura et al., Nature 350:512–515, 1991.
Rosenberg et al., BIOSIS Abstract, pp. 9638–8642, Abstract No. 93018797 Proceedings of the National Academy of Sciences, vol. 88, 1991.
Rosenberg et al., BIOSIS Abstract, pp. 449–454, Abstract No. 91131959 Oncogene, vol. 6, 1991.
Withers et al., Molecular and Cellular Biology 11:4846–4853, 1991.
Xiong et al., Cell 65:691–699, 1991.

*Primary Examiner*—Marianne P. Allen
*Attorney, Agent, or Firm*—Sterne, Kessler, Goldstein & Fox P.L.L.C.

[57] ABSTRACT

A novel cyclin termed prad1, including human prad1; an antibody specific for prad1; a nucleic acid sequence which encodes prad1 or a portion of prad1; and methods of using such antibody or nucleic acid to diagnose a neoplastic condition characterized by overexpression of prad1.

28 Claims, 18 Drawing Sheets

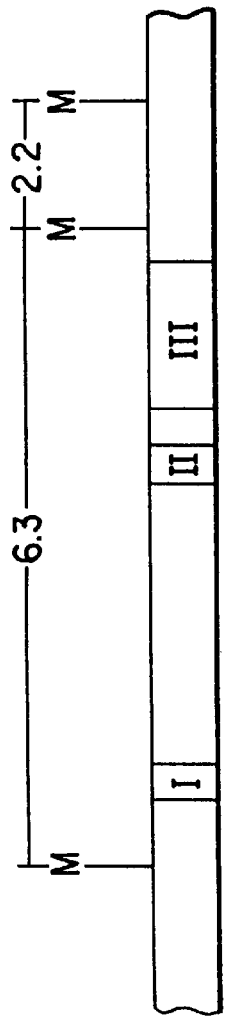
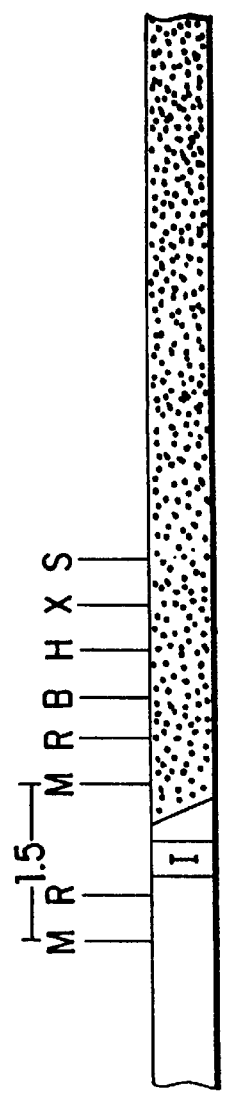
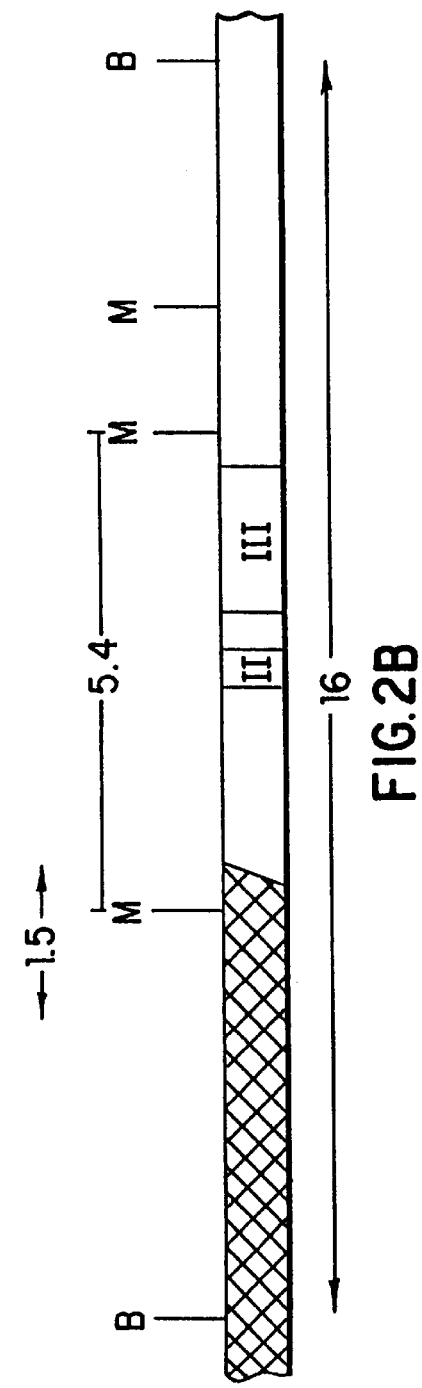
FIG. 2A
FIG. 2B

```
GGCGCAGTAG CAGGAGCAG CAGAGTCCGC ACGTCCGGC GAGGGGCAGA AGAGCGGGAG         60

GGAGCGCGGG GCAGCAGAAG CGAGAGCCGA GCGCGGACCC AGCCAGGACC CACAGCCCTC        120

CCCAGCTGCC CAGGAAGAGC CCCAGCC ATG GAA CAC CAG CTC CTG TGC TGC            171
                              Met Glu His Gln Leu Leu Cys Cys
                               1               5

GAA GTG GAA ACC ATC CGC CGC GCG TAC CCC GAT GCC AAC CTC CTC AAC          219
Glu Val Glu Thr Ile Arg Arg Ala Tyr Pro Asp Ala Asn Leu Leu Asn
     10                  15                  20

GAC CGG GTG CTG CGG GCC ATG CTG AAG GCG GAG ACC TGC GCG CCC              267
Asp Arg Val Leu Arg Ala Met Leu Lys Ala Glu Thr Cys Ala Pro
 25                  30                  35              40

TCG GTG TCC TAC TTC AAA TGT GTG CAG AAG GAG GTC CTG CCG TCC ATG          315
Ser Val Ser Tyr Phe Lys Cys Val Gln Lys Glu Val Leu Pro Ser Met
             45                  50                  55

CGG AAG ATC GTC GCC ACC TGG ATG CTG GAG GTC TGC GAG GAA CAG AAG          363
Arg Lys Ile Val Ala Thr Trp Met Leu Glu Val Cys Glu Glu Gln Lys
         60                  65                  70

TGC GAG GAG GTC TTC CCG CTG GCC ATG AAC TAC CTG GAC CGC TTC              411
Cys Glu Glu Val Phe Pro Leu Ala Met Asn Tyr Leu Asp Arg Phe
 75                  80                  85
```

FIG.6A

```
CTG TCG CTG GAG CCC GTG AAA AAG AGC CGC CTG CAG CTG GGG GCC        459
Leu Ser Leu Glu Pro Val Lys Lys Ser Arg Leu Gln Leu Gly Ala
         90                  95                 100

ACT TGC ATG TTC GTG GCC TCT AAG ATG AAG GAG ACC ATC CCC CTG ACG    507
Thr Cys Met Phe Val Ala Ser Lys Met Lys Glu Thr Ile Pro Leu Thr
         105                 110                 115            120

GCC GAG AAG CTG TGC ATC TAC ACC GAC AAC TCC ATC CGG CCC GAG GAG    555
Ala Glu Lys Leu Cys Ile Tyr Thr Asp Asn Ser Ile Arg Pro Glu Glu
         125                 130                 135

CTG CTG CAA ATG GAG CTG CTC CTG GTG AAC AAG CTC AAG TGG AAC CTG    603
Leu Leu Gln Met Glu Leu Leu Leu Val Asn Lys Leu Lys Trp Asn Leu
         140                 145                 150

GCC GCA ATG ACC CCG CAC GAT TTC ATT GAA CAC TTC CTC TCC AAA ATG    651
Ala Ala Met Thr Pro His Asp Phe Ile Glu His Phe Leu Ser Lys Met
         155                 160                 165

CCA GAG GAG GAG AAC AAA CAG ATC ATC CGC AAA CAC GCG CAG ACC        699
Pro Glu Glu Glu Asn Lys Gln Ile Ile Arg Lys His Ala Gln Thr
         170                 175                 180

TTC GTT GCC CTC TGT GCC ACA GAT GTG AAG TTC ATT TCC AAT CCG CCC    747
Phe Val Ala Leu Cys Ala Thr Asp Val Lys Phe Ile Ser Asn Pro Pro
         185                 190                 195            200
```

FIG. 6B

```
TCC ATG GTG GCA GCG GGG AGC GTG GTG GCC GCA GTG CAA GGC CTG AAC         795
Ser Met Val Ala Ala Gly Ser Val Val Ala Ala Val Gln Gly Leu Asn
            205                     210                     215

CTG AGG AGC CCC AAC AAC TTC CTG TCC TAC TAC CGC CTC ACA CGC TTC         843
Leu Arg Ser Pro Asn Asn Phe Leu Ser Tyr Tyr Arg Leu Thr Arg Phe
            220                     225                     230

CTC TCC AGA GTG ATC AAG TGT GAC CCA GAC TGC CTC CGG GCC TGC CAG         891
Leu Ser Arg Val Ile Lys Cys Asp Pro Asp Cys Leu Arg Ala Cys Gln
            235                     240                     245

GAG CAG ATC GAA GCC CTG CTG CTG GAG TCA AGC CTG CGC CAG GCC CAG CAG     939
Glu Gln Ile Glu Ala Leu Leu Leu Glu Ser Ser Leu Arg Gln Ala Gln Gln
            250                     255                     260

AAC ATG GAC CCC AAG GCC GCC GAG GAG GAA GAG GAG GAG GAG GAG GAG         987
Asn Met Asp Pro Lys Ala Ala Glu Glu Glu Glu Glu Glu Glu Glu Glu
            265                     270                     275             280

GTG GAC CTG GCT TGC ACA CCC ACC GAC GTG CGG GAC GTG GAC ATC TGA        1035
Val Asp Leu Ala Cys Thr Pro Thr Asp Val Arg Asp Val Asp Ile
            285                     290                     295

GGGGCCCAGG CAGGCGGGGCG CCACCGCCAC CCGCAGCGAG GGCGGAGCCG GCCCCAGGTG     1095

CTCCACTGAC AGTCCCTCCT CTCCGGAGCA TTTTGATACC AGAAGGGAAA GCTTCATTCT      1155
```

FIG.6C

```
CCTTGTTGTT GGTTGTTTTT TCCTTTGCTC TTTCCCCCTT CCATCTCTGA CTTAAGCAAA    1215

AGAAAAAGAT TACCCAAAAA CTGTCTTTAA AAGAGAGAGA GAGAAAAAAA AAATAGTATT    1275

TGCATAACCC TGAGCGGTGG GGGAGGAGGG TTGTGCTACA GATGATAGAG GATTTTATAC    1335

CCCAATAATC AACTCGTTTT TATATTAATG TACTTGTTTC TCTGTTGTTA GAATAGGCAT    1395

TAACACAAAG GAGGGGTCTC GGGAGAGGAT TAGGTTCCAT CCTTTACGTG TTTAAAAAAA    1455

AGCATAAAAA CATTTTAAAA ACATAGAAAA ATTCAGCAAA CCATTTTTAA AGTAGAAGAG    1515

GGTTTTAGGT AGAAAAACAT ATTCTTGTGC TTTTCCTGAT AAAGCACAGC TGTAGTGGGG    1575

TTCTAGGCAT CTCTGTACTT TGCTTGCTCA TATGCATGTA ACCTCTTCAC AAGTCATTGT    1635

ATGTTATTAT ATTCCGTAGG TAGATGTGTA ACCTCTTCAC CTTATTCATG GCTGAAGTCA    1695

CCTCTTGGTT ACAGTAGCGT AGCGGTGGCCG ACAAACCATC CTTTGGGCCT GTGACCACCA    1755

CCCCAACAAA CCATCCAGTG ACAAACCATC CAGTGGAGGT TTGTCGGGCA CCAGCCAGCG    1815

TAGCAGGGTC GGGAAAGGCC ACCTGTCCCA CTCCTACGAT ACGCTACTAT AAAGAGAAGA    1875

CGAAATAGTG ACATAATATA TTCTATTTTT ATACTCTTCC TATTTTTGTA GTGACCTGTT    1935

TATGAGATGC TGGTTTTCTA CCCAACGGCC CTGCAGCCAG CTCACGTCCA GGTTCAACCC    1995
```

FIG.6D

```
ACAGCTACTT GGTTTGTGTT CTTCTTCATA TTCTAAAACC ATTCCATTTC CAAGCACTTT  2055

CAGTCCAATA GGTGTAGGAA ATAGCGCTGT TTTTGTTGTG TGTGCAGGGA GGGCAGTTTT  2115

CTAATGGAAT GGTTTGGGAA TATCCATGTA CTTGTTTGCA AGCAGGACTT TGAGGCAAGT  2175

GTGGGCCACT GTGGTGGCAG TGGAGGTGGG GTGTTTGGGA GGCTGCGTGC CAGTCAAGAA  2235

GAAAAAGGTT TGCATTCTCA CATTGCCAGG ATGATAAGTT CCTTTCCTTT TCTTTAAAGA  2295

AGTTGAAGTT TAGGAATCCT TTGGTGCCAA CTGGTGTTTG AAAGTAGGGA CCTCAGAGGT  2355

TTACCTAGAG AACAGGTGGT TTTTAAGGGT TATCTTAGAT GTTCACACCC GGAAGGTTTT  2415

TAAACACTAA AATATATAAT TTATAGTTAA GGCTAAAAAG TATATTTATT GCAGAGGATG  2475

TTCATAAGGC CAGTATGATT TATAAATGCA ATCTCCCCTT GATTTAAACA CACAGATACA  2535

CACACACACA CACACACACA CACAAACCTT CTGCCTTTGA TGTTACAGAT TTAATACAGT  2595

TTATTTTTAA AGATAGATCC TTTTATAGGT GAGAAAAAAA CAATCTGGAA GAAAAAAACC  2655

ACACAAAGAC ATTGATTCAG CCTGTTTGGC GTTTCCCAGA GTCATCTGAT TGGACAGGCA  2715

TGGGTGCAAG GAAAATTAGG GTACTCAACC TAAGTTCGGT TCCGATGAAT TCTTATCCCC  2775

TGCCCCTTCC TTTAAAAAAC TTAGTGACAA AATAGACAAT TTGCACATCT TGGCTATGTA  2835
```

FIG. 6E

```
ATTCTTGTAA TTTTTATTTA GGAAGTGTTG AAGGGAGGTG GCAAGAGTGT GGAGGCTGAC  2895

GTGTGAGGGA GGACAGGCGG GAGGAGGTGT GAGGAGGAGG CTCCCGAGGG GAAGGGGCGG  2955

TGCCCACACC GGGGACAGGC CGCAGCTCCA TTTTCTTATT GCGCTGCTAC CGTTGACTTC  3015

CAGGCACGGT TTGGAAATAT TCACATCGCT TCTGTGTATC TCTTTCACAT TGTTTGCTGC  3075

TATTGGAGGA TCAGTTTTTT GTTTTACAAT GTCATATACT GCCATGTACT AGTTTTAGTT  3135

TTCTCTTAGA ACATTGTATT ACAGATGCCT TTTTTGTAGT TTTTTTTTTT TTTATGTGAT  3195

CAATTTTGAC TTAATGTGAT TACTGCTCTA TTCCAAAAAG GTTGCTGTTT CACAATACCT  3255

CATGCTTCAC TTAGCCATGG TGGACCCAGC GGGCAGGTTC TGCCTGCTTT GGCGGGCAGA  3315

CACGCGGGCG CGATCCCACA CAGGCTGGCG GGGGCCGGCC CCGAGGCCGC GTGCGTGAGA  3375

ACCGCGCCGG TGTCCCCAGA GACCAGGCTG TGTCCCTCTT CTCTTCCCTG CGCCTGTGAT  3435

GCTGGGCACT TCATCTGATC GGGGGCGTAG CATCATAGTA GTTTTTACAG CTGTGTTATW  3495

CTTTGCGTGT AGCTATGGAA GTTGCATAAT TATTATTATT ATTATTATAA CAAGTGTGTC  3555

TTACGTGCCA CCACGGCGTT GTACCTGTAG GACTCTCATT CGGGATGATT GGAATAGCTT  3615

CTGGAATTTG TTCAAGTTTT GGGTATGTTT AATCTGTTAT GTACTAGTGT TCTGTTTGTT  3675
```

FIG.6F

```
ATTGTTTTGT TAATTACACC ATAATGCTAA TTTAAAGAGA CTCCAAATCT CAATGAAGCC    3735
AGCTCACAGT GCTGTGTGCC CCGGTCACCT AGCAAGCTGC CGAACCAAAA GAATTTGCAC    3795
CCCGGCTGCGG GCCCACGTGG TTGGGGCCCT GCCCTGGCAG GGTCATCCTG TGCTCGGAGG   3855
CCATCTCGGG CACAGGCCCA CCCCGCCCCA CCCCTCCAGA ACACGGCTCA CGCTTACCTC    3915
AACCATCCTG GCTGCGGGCGT CTGTCTGAAC CACGCGGGGG CCTTGAGGGA CGCTTTGTCT   3975
GTCGTGATGG GGCAAGGGCA CAAGTCCTGG ATGTTGTGTG TRTCGAGAGG CCAAAGGCTG    4035
GTGGCAAGTG CACGGGGCAC AGCGGAGTCT GTCCTGTGAC GCGCAAGTCT GAGGGTCTGG    4095
GCGGGGGGCG GCTGGGTCTG TGCATTTCTG GTTGCACCGC GGGCTTCCC AGCACCAACA     4155
TGTAACCGGC ATGTTTCCAG CAGAGAGACAA AAAGACAAAC ATGAAAGTCT AGAAATAAAA   4215
CTGGTAAAAC CCCAAAAAAA AAAAAAAA                                        4244
```

FIG.6G

```
human cyclin A:   MRAILVDWLVEVGEEYKLQNETLHLAVNYIDRFLSSMSVLRGKLQLVGTAAMLLASKFEEIYPPEVAEFVYITDDTYTK    288
                  || |* |**|||| |**| |*|*|||| |**|||||| *| ***|||||** | *||    ]|
pradl:            MRKIVATWMLEVCEEQKCEEEVFPLAMNYLDRFLSLEPVKKSRLQLLGATCMFVASKMKETIPLTAEKLCIYTDNSIRP    134
                  || |* |**||| |*    |**||||||| * ***||||||| *||*|  ||*|*|                 ]|** *
clam cyclin A:    MRCILVDWLVEVSEEDKLHRETLFLGVNYIDRFLSKISVLRGKLQLVGAASMFLAAKYEEIYPPDVKEFAYITDDTYTS    273 human cyclin A:   KQVLRMEHLVLKVLTFDLAAPTVNQFLTQYFLHQQPANCKVESL...AMFLGELSLIDADPYLKYLPSVIAGAA         359
                  |  ||| | ||| | * **||  * *      |  * *        |||***
pradl:            EELLQMELLLVNKLKWNLAAMTPHDFIEHFLSKMPEAEENKQIIRKHAQTFVALCATDVK.FISNPPSMVAAGS         207
                  ***||||| |* |***|| |*      |*||   ** * |*|**  *  **  *| ||**
clam cyclin A:    QQVLRMEHLILKVLTFDVAVPTTNWFCEDFL.KSCDADDK...LKSLTMFLTELTLIDMDAYLKYLPSITAAAA         343 human cyclin B:   MRAILIDWLVQVQMKFRLLQETMYMTVSIIDRFMQNNCVPKKMLQLVGVTAMFIASKYEEMYPPEIGDFAFVTDNTYTK    279
                  |||  |***| |  *|  * *|     *** *|||| *|||| |* |||| *||||*|| | |*|        ]||*
pradl:            MRKIVATWMLEVCEEQKCEEEVFPLAMNYLDRFLSLEPVKKSRLQLLGATCMFVASKMKETIPLTAEKLCIYTDNSIRP    134
                  || |** *||| |*    *||||||||      *|||*|*|||  |  *|*|  |*| *   ||*|
cdc13:            MRGILTDWLIEVHSRFRLLPETLFLAVNIIDRFLSRVCSLNKLQLVGIAALFIASKYEEVMCPSVQNFVYMADGGYDE     313 human cyclin B:   HQIRQMEMKILRALNFGLGRPLPLHFLRR.ASKIGEVDVEQHTL...AKYLMELTMLDYDMVHFPPSQIAAGA         348
                  **  |||| |* |* |*    |*   **      |*  * ***      *|     *  * |||  *||||*
pradl:            EELLQMELLLVNKLKWNLAAMTPHDFIEHFLSKMPEAEENKQIIRKHAQTFVALCATDVKFISNPPSMVAAGS         207
                  ||*||  **  *|||     |  |* |   ** |*  |*** |*        |* |*  ||  |||| |**
cdc13:            EEILQAERYILRVLEFNLAYPNPMN....FLRRISKADFYDIQTRTVAKYLVEIGLLDHKLLPYPPSQQCAAA         382 pradl:            MRKIVATWMLEVCEEQKCEEEVFPLAMNYLDRFLSLEPVKKSRLQLLGATCMFVASKMKETIPLTA......EKLCIYTD  129
                  ||  *   * |  |* |  | |||||   ||*   * ||* |* ****|||  |      * ||    *
cln3:             MRFLIFDFIMYCHTRLNLSTSTLFLTFTILDKYSSRFIIKSYNYQLLSLTALWISSKFWDSKNRMATLKVLQNLC.CNQ   184 pradl:            NSIRPEELLQMELLLVNKLKWNLAAMTPHD.FIEHFLSKMPEAEENKQIIRKHAQTFVALCATDVKFISNPPSMVAAGS   207
                  ||* *   ||*|  |** ||*|| |* *||   * *     **   * * |*|** *||***
cln3:             YSIK..QFTTMEMHLFKSLDWSICQSATFDSYIDIFLFQSTSPLSPGVVL...SAPLEAFIQQKLALLNNAAGTAINKS   258
```

FIG. 7

PRAD1 CYCLIN AND ITS CDNA

BACKGROUND OF THE INVENTION

Partial funding for the work described herein was provided by the U.S. Government, which has certain rights in the invention.

This invention relates to the field of cyclins.

The cyclins are a class of eukaryotic proteins that were originally identified by their cyclic accumulation and destruction at defined points in embryonic cell cycles (Evans et al., Cell 33:389–396, 1983). They bind to and are essential for activation of cdc2 protein kinase (reviewed in Murray et al., Science 246:614–621, 1989; Nurse, Nature 344:503–508, 1990; Draetta et al., Cell 56:829–838, 1989). At present, the cyclins can be divided into three families on the basis of their kinetics of oscillation across the cell cycle, their amino acid sequences, and, in some cases, genetic experiments in yeast that determine when their functions are needed (reviewed in Nurse, 1990; Nasmyth, Cell 63:1117–1120, 1990; Westendorf, J. Cell Biol. 108:1431–1444, 1989). The B-type "mitotic" cyclins drive cells into mitosis; their sequences are conserved from yeast to human (Nurse, 1990; Westendorf et al., 1989; and Pines et al., Cell 58:833–846, 1989). The A-type cyclins, which are less well understood, may act earlier in the cell cycle (Minshull et al., EMBO J. 9:2865–2875, 1990; Pines et al., Nature 346:760–763, 1990; Swenson et al., Cell 47:861–870, 1986). The recently described CLNs (or "G1 cyclins") of budding yeast are thought to perform analogous functions by interacting with cdc2 homologues at START, driving cells into S-phase (Nasmyth, 1990). A, B, and CLN cyclins may act as stage-specific regulators of progress across the cell cycle by conferring selective substrate specificity upon cdc2 kinase (Minshull et al., 1990) or by selectively targeting cdc2 to different intracellular compartments.

SUMMARY OF THE INVENTION

The invention features a novel cyclin, prad1, and an isolated DNA (termed PRAD1) which encodes it. This DNA may be single-stranded or double-stranded, and may be genomic DNA, cDNA, or synthetic DNA. It may be identical to a naturally-occurring PRAD1 sequence (such as human PRAD1 cDNA, SEQ ID NO:1) or may differ from such sequence by the deletion, addition, or substitution of one or more nucleotides. By "isolated" is meant that the DNA is free of the coding sequences of genes that, in the naturally-occurring genome of the organism from which the DNA of the invention is derived, immediately flank the gene encoding prad1. Included within the term prad1 is human prad1 (SEQ ID NO.2) and any homolog of human prad1 (i.e., from another animal species, or a genetically altered version of a naturally-occurring prad1 which exhibits a biological activity similar to that of the naturally-occurring protein) encoded by a DNA which is capable of hybridizing (1) under stringent hybridization conditions (Sambrook et al., Molecular Cloning: A Laboratory Manual, 2nd edn., Cold Spring Harbor, N.Y., 1989: herein incorporated by reference) to a single-stranded probe consisting of a segment of at least eight (preferably 18–40) nucleotides of human PRAD1 cDNA (SEQ ID NO:1) or human PRAD1 genomic DNA, or (2) under less stringent conditions (e.g., washing at 2×SSC, at 40° C.) to a probe consisting of a segment of at least 40 (preferably 200–5000) nucleotides of human PRAD1 cDNA (SEQ ID NO:1) or human PRAD1 genomic DNA. Also within the invention are peptide fragments of a naturally-occurring prad1, which fragments are at least six amino acids in length and preferably 10–50 amino acids; and single-stranded DNA or RNA probes (preferably radioactively labelled) containing at least 8 nucleotides of, but less than all of, human PRAD1-encoding RNA, human PRAD1 cDNA (SEQ ID NO:1) or human PRAD1 genomic DNA, and preferably between 10 and 5000 bases. Such DNA or RNA probes may be used in a diagnostic method which includes the steps of obtaining a nucleic acid sample from an animal suspected of having a given neoplastic condition (or from a known tumor); contacting the nucleic acid sample with a single-stranded DNA or RNA probe capable of hybridizing to the PRAD1 homolog of the species to which the animal belongs; and detecting the level of hybridization of the probe with the nucleic acid sample, such level being diagnostic for the neoplastic condition. Two examples of neoplastic conditions that may be diagnosed by this method include centrocytic lymphomas, which appear to express abnormally high levels of PRAD1 mRNA, and those breast cancers which are characterized by a high degree of amplification of PRAD1 DNA.

The DNA sequence of the invention, which may be under the transcriptional control of a heterologous promoter (defined as a promoter sequence other than the naturally-occurring promoter of the gene encoding prad1), may be incorporated into a vector (such as a phage) and thereby introduced into a cell. Included within the invention is a eukaryotic or prokaryotic cell (or an essentially homogeneous population of such cells) containing (and preferably capable of expressing) a recombinant DNA molecule encoding prad1: that is, a cell into which (or into an ancestor of which) has been introduced, by means of genetic engineering, a DNA molecule encoding prad1, resulting in that DNA molecule's being positioned adjacent to a DNA sequence to which it is not naturally adjacent (e.g., the prad1-encoding sequence is integrated into the genome of such cell). The prad1 protein of the invention may be produced by culturing such cells and recovering prad1 from the cells, or from their medium. Alternatively, DNA or mRNA encoding prad1 may be combined with a standard in vitro expression system to produce prad1. Prad1 so produced can be utilized in combination with a pharmacologically-acceptable carrier to promote wound healing in an animal, or can be used to promote proliferation of an animal cell by treating the cell with a proliferation-inducing amount of the protein of the invention (for example, by transfecting the cell with DNA encoding prad1 so that the cell itself produces such a proliferation-inducing amount of prad1). Alternatively, the prad1 (or an antigenic fragment thereof, determined by standard methodology) can be used to raise polyclonal or monoclonal antibodies capable of forming immune complexes with prad1, and thus useful as a diagnostic for certain neoplastic conditions characterized by abnormally high levels of prad1 expression. The method of using such an antibody as a diagnostic would include the steps of obtaining a sample of a tissue of an animal suspected of having a such a neoplastic condition (e.g., certain lymphomas or breast cancers); contacting the sample with the antibody; and detecting the level of immune complexes formed by the antibody, such level being diagnostic for the neoplastic condition.

Also within the invention is a transgenic non-human vertebrate animal (preferably a mammal such as a rodent, e.g., a mouse) bearing a transgene (i.e., a piece of DNA which is artificially inserted into an embryonic cell, and becomes a part of the genome of the animal which develops from that cell) which includes a DNA sequence encoding prad1, and any cells or cell lines derived from such an animal. A transgenic animal is an animal having cells that contain a transgene, which transgene was introduced into the animal, or an ancestor of the animal, at an embryonic stage. If the embryonic stage is a single-cell stage, then all nucleated cells of the animal will carry the transgene. The particular prad1 encoded by the transgene may be endogenous to the species of the transgenic animal, or may be that of a different species (e.g., human). By using a PRAD1 together with an appropriate promoter, a transgenic animal which readily develops neoplasias in a selected organ or tissue type will result, making such animal useful as a model for studying cancer in that organ or tissue.

Other features and advantages of the invention will be apparent from the following detailed description, and from the claims.

DETAILED DESCRIPTION

The drawings are first described.

Drawings

FIG. 1 is a Southern blot of Msp1-digested DNA probed with the 5' PTH gene probe (lanes 1, 2) and 3' PTH gene probe (lanes 3, 4).

FIG. 2A is a diagrammatic representation of the normal PTH gene, and FIG. 2B, the two fragments resulting from the rearrangement in tumor M.

FIGS. 5A–D are a diagrammatic representation of PTH/D11S287 rearrangements in two parathyroid adenomas, and the relative locations of Probe B and a series of cloned cDNA segments.

FIGS. 6A–6G are a representation of the nucleotide sequence and predicted amino acid sequence of human PRAD1 (SEQ ID NO:1) cDNA.

FIG. 7 is an illustration of sequence homology between the "cyclin box" region of human prad1 (SEQ ID NO.4) and the corresponding regions of some A-type, B-type, and G1 cyclins.

Figure 8:
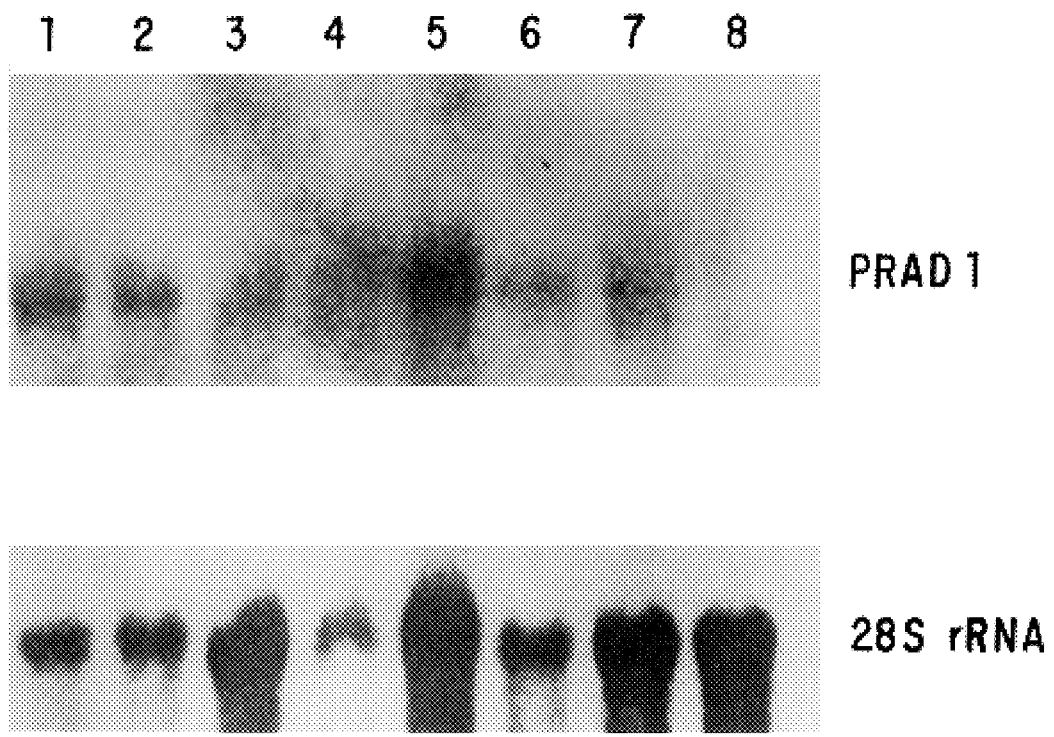

FIG. 8 is a Northern blot analysis of D11S287 [human PRAD1 (SEQ ID NO:1)] expression in various cell types.

Figure 9A:
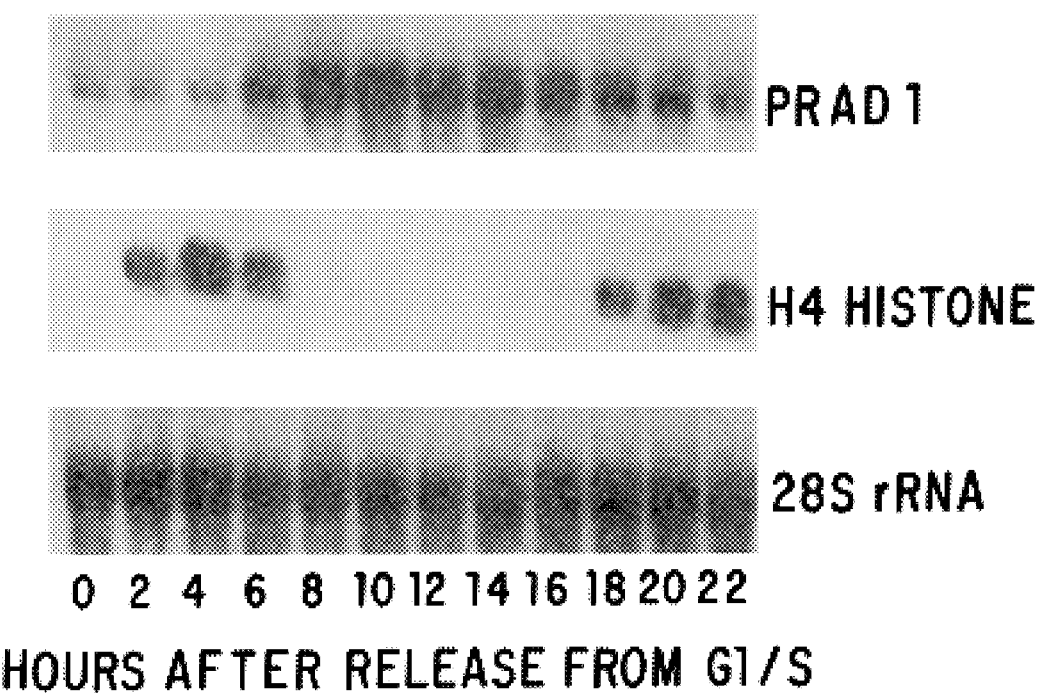
Figure 9B:
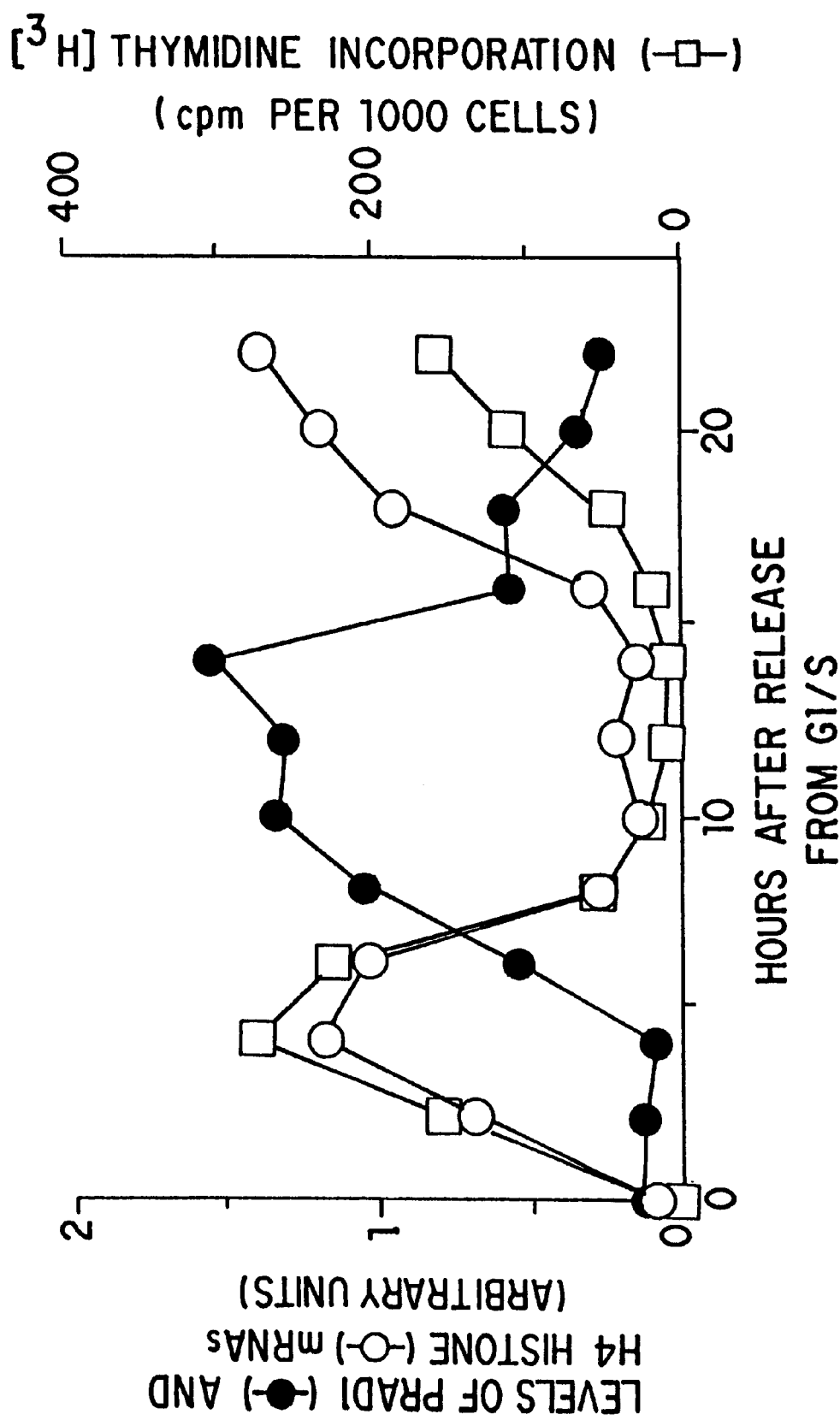
Figure 10A:
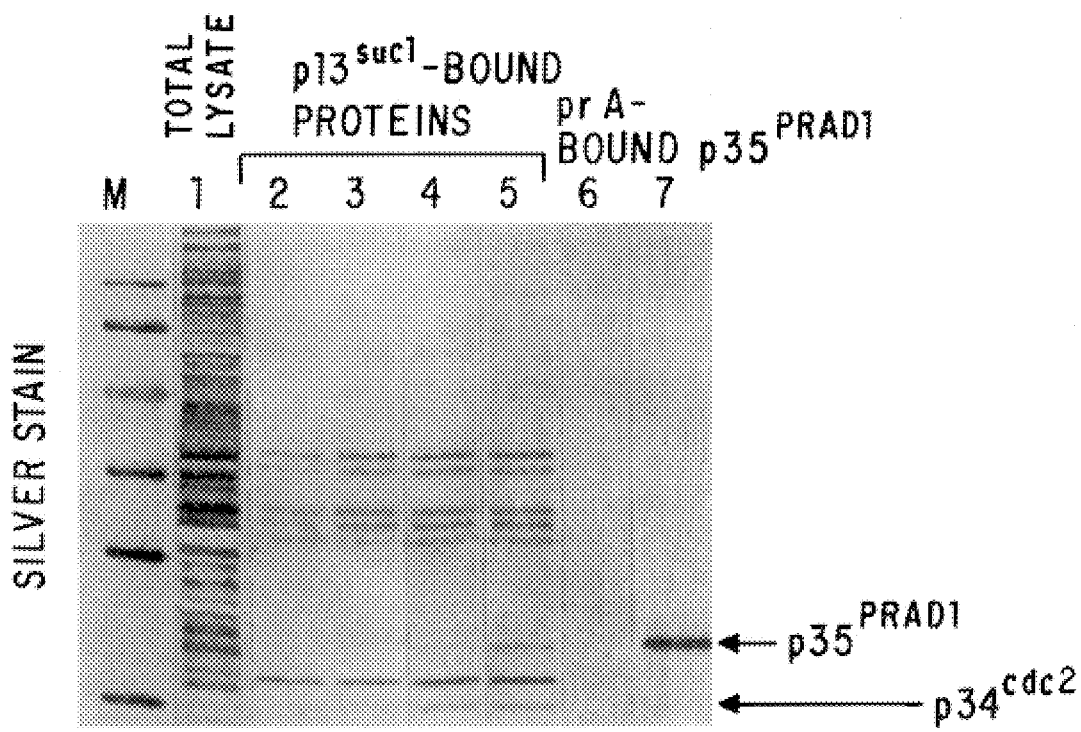
Figure 10B:
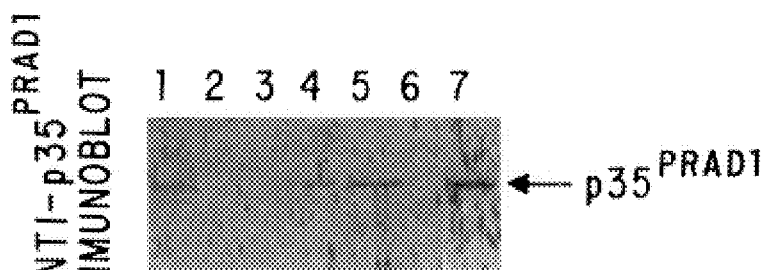
Figure 10C:
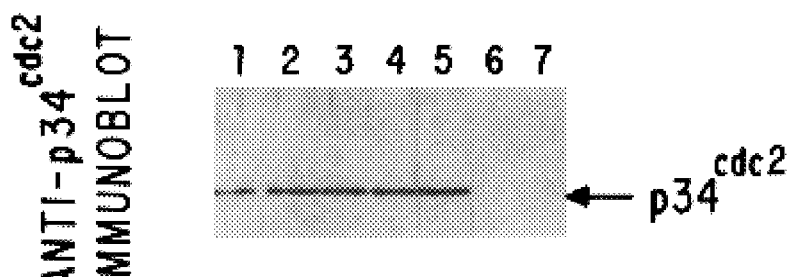
Figure 10D:
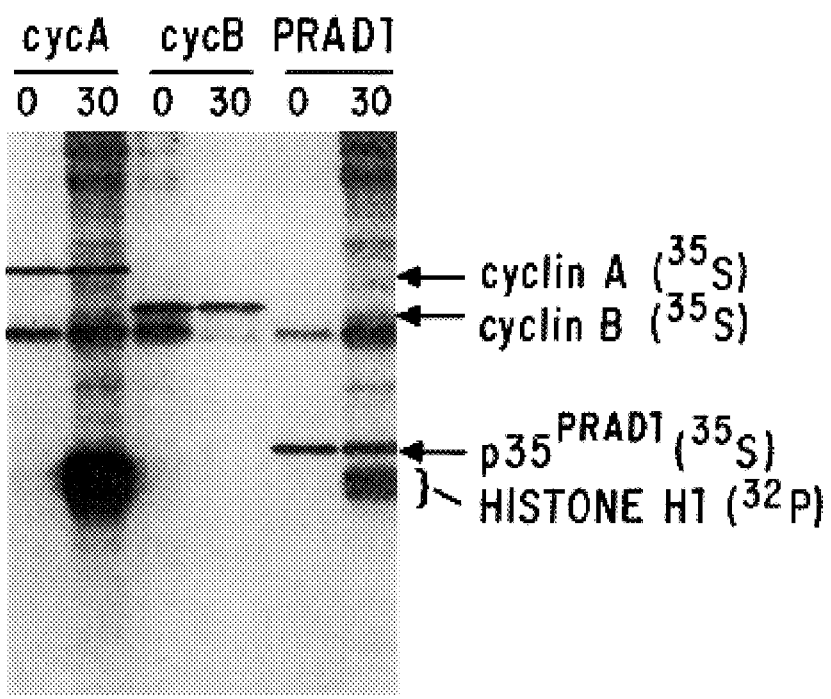

FIG. 9A is a Northern blot analysis of HeLa cell RNA probed with a human PRAD1 cDNA (SEQ ID NO:1) probe, an H4 histone probe, and 28S rRNA; and FIG. 9B, a graph depicting the results of the Northern blot.

FIGS. 10A–D are an analysis of the biological activity of recombinant human prad1.

IDENTIFICATION OF HUMAN PRAD1

Previous studies on DNA from cells of a benign parathyroid adenoma (reported in Arnold et al., J. Clin. Invest. 83:2034–2040, 1989) revealed evidence of a DNA rearrangement involving the parathyroid hormone (PTH) chromosomal locus (at chromosome 11, band p15) and a segment of DNA (identified as Human Genome Database assignment D11S287) which normally maps to chromosome 11, band q13. It is now known that (a) although a number of previously-identified oncogenes (including INT-2 and HST-1), as well as the translocation breakpoint marker BCL-1 and possibly the gene for multiple endocrine neoplasia type I (MEN-I), map to the 11q13 region, the so-called D11S287 locus rearranged in at least some parathyroid adenomas is distinct from these previously-described markers; (b) D11S287 mRNA, while detectable in all tissues analyzed, is significantly overexpressed in those parathyroid adenomas which have a 11q13/11p15 chromosomal rearrangement, and also in certain lymphomas (notably centrocytic lymphomas) characterized by rearrangement of the BCL-1 locus; and (c) the D11S287 locus is amplified and expressed in many squamous cell and mammary carcinomas. This evidence suggests that D11S287 (also referred to herein as human PRAD1, for parathyroid adenoma) is a newly-identified oncogene which figures in a variety of types of neoplasms.

Cloning Human PRAD1 cDNA (SEQ ID NO:1)

Human PRAD1 cDNA (SEQ ID NO: 1) has been cloned and sequenced by the methods described in detail below, yielding the sequence shown in FIG. 6. The longest open reading frame, starting at the first ATG codon, encodes a predicted protein of 295 amino acids ($M_r$ 33,729) (SEQ ID NO.2). Screening the Genbank peptide database with this sequence reveals significant homology only to members of the cyclin family, with greatest similarity in the region conserved among cyclins, ranging from 19.1% to 33.6% identity, and 44.1% to 59.2% similarity. The human PRAD1 (SEQ ID NO:1) protein (prad1) has significant sequence similarities to all three types of cyclins (A, B, and CLN cyclins), but cannot readily be assigned to any one type. This suggests that prad1 may represent a new and different cyclin family member.

PRAD1 Expression

PRAD1 mRNA is expressed in many tissues and is highly conserved across species (FIG. 7). As with other cyclin mRNAs expressed in human cells (Pines et al., Cell 58:833–846, 1989; Pines et al., Nature 346:760–763, 1990), human PRAD1 mRNA levels vary across the cell cycle (FIG. 9), consistent with but not proving a role in cell cycle regulation. The peak in PRAD1 mRNA levels occurs late in the cell cycle or in G1.

Biological Activity of Recombinant Human Prad1 Protein

Bacterially expressed recombinant human prad1 (SEQ ID NO.2), produced as described in detail below, was used to further investigate the link between human PRAD1 and the cyclins. Cyclins are known to form complexes with $p34^{cdc2}$ protein kinase, leading to its activation which can be assayed using exogenous histone H1 as a substrate. In addition, cyclin/$p34^{cdc2}$ complexes can be purified by exploiting the ability of beads linked to $p13^{suc1}$, another cell cycle protein, to avidly bind $p34^{cdc2}$ and, in turn, co-purify any proteins complexed with $p34^{cdc2}$ (Draetta et al., Cell 56:829–838, 1989). When recombinant human prad1 (SEQ ID NO.2) was added to clam embryo interphase cell lysates (which lack endogenous cyclins and contain inactive $p34^{cdc2}$), both $p34^{cdc2}$ and prad1 were bound by $p13^{suc1}$-beads (FIG. 10). As prad1 does not bind to protein A-Sepharaose beads, its binding to $p13^{suc1}$-beads is most likely due to its interaction with $p34^{cdc2}$ or a closely related protein. Furthermore, kinase activity was induced by the addition of the human PRAD1 (SEQ ID NO:1) in vitro translation product to interphase lysates (FIG. 10). This kinase activity was lower than that seen with cyclin A. Cyclin B provided a negative control; for reasons not yet understood, our cyclin B translation product was not capable of activating $p34^{cdc2}$ in this type of assay. The difference between the activities induced by cyclin A and human prad1 (SEQ ID NO.2) may be specific to this clam assay system, or may reflect a genuine difference between the functions of, or the substrate specificities conferred by, cyclin A vs. human prad1(SEQ ID NO.2).

Use

Both prad1 and a nucleotide encoding prad1 are useful for the preparation of diagnostic tools for the classification and/or prognosis of lymphomas, breast cancers, and squamous cell cancers, as well as other cancers characterized by a high level of expression and/or amplification of the PRAD1 gene. For example, prad1 or an antigenic peptide fragment of prad1 could be used in accordance with standard methods (see, e.g., Harlow et al., *Antibodies: A Laboratory Manual*, Cold Spring Harbor Laboratory, Cold Spring Harbor, N.Y., 1988; Yanaihara et al., U.S. Pat. No. 4,855,406; and Slamon et al., U.S. Pat. No. 4,918,162; all of which are herein incorporated by reference) to raise polyclonal or monoclonal antibodies capable of forming immune complexes with prad1, and useful for detecting abnormally high levels of prad1 in a given tissue sample. Similarly, a hybridization probe prepared from a segment of at least 12 (and preferably greater than 250) nucleotides of human PRAD1-encoding RNA, human PRAD1 cDNA (SEQ ID NO:1) or human PRAD1 genomic DNA may be employed as a means for determining the number of copies of PRAD1 present in the genomic DNA of a given sample, or the level of PRAD1 mRNA expressed in cells of such sample.

The nucleic acids of the invention may also be used therapeutically. Oligonucleotides which are antisense to human PRAD1 mRNA (or which express RNA that is antisense to human PRAD1 mRNA) may be synthesized to serve as an anticancer therapy in those cases diagnosed as having a rearrangement or amplification of human PRAD1: such oligonucleotides would be introduced into tumor cells in vivo as a means to reduce production of prad1 in such cells, and thereby to reduce neoplastic growth induced by an overabundance of prad1. (See, for example, Weinberg et al., U.S. Pat. No. 4,740,463, herein incorporated by reference.). By linking a PRAD1 sequence to a selected tissue-specific promoter or enhancer and introducing by standard methods (e.g., as described by Leder et al., U.S. Pat. No. 4,736,866, herein incorporated by reference) the resultant hybrid gene into an animal embryo at an early developmental stage (e.g., the fertilized oocyte stage), a transgenic animal which expresses elevated levels of prad1 in the selected tissue (e.g., breast, squamous cell, B-lymphoid cell, parathyroid, and others) can be produced. The form of PRAD1 utilized can be one which encodes a prad1 similar to that of the animal species used, or it can encode the prad1 homolog of a different species (e.g., human). Such an animal would be useful as an in vivo model for neoplastic disease in the selected tissue. In addition, cells derived from such a transgenic animal may be used to establish an immortal cell line that retains at least some of its differentiated characteristics while proliferating indefinitely in vitro. Alternatively, one could stably transfect primary cells (e.g., a type that has proven difficult to maintain in culture, such as pituitary cells) with a PRAD1 gene linked to an appropriate promoter (e.g., the metallothionin promoter) which ensures high levels of expression of the gene, and thereby establish an immortal cell line derived from such primary cells. PRAD1 sequences may be particularly useful in this regard because overexpression of PRAD1 (at least in parathyroid tissues) appears to trigger the proliferation of normally quiescent cells without causing them to completely lose their differentiated phenotype.

Experimental Data

Figure 1:
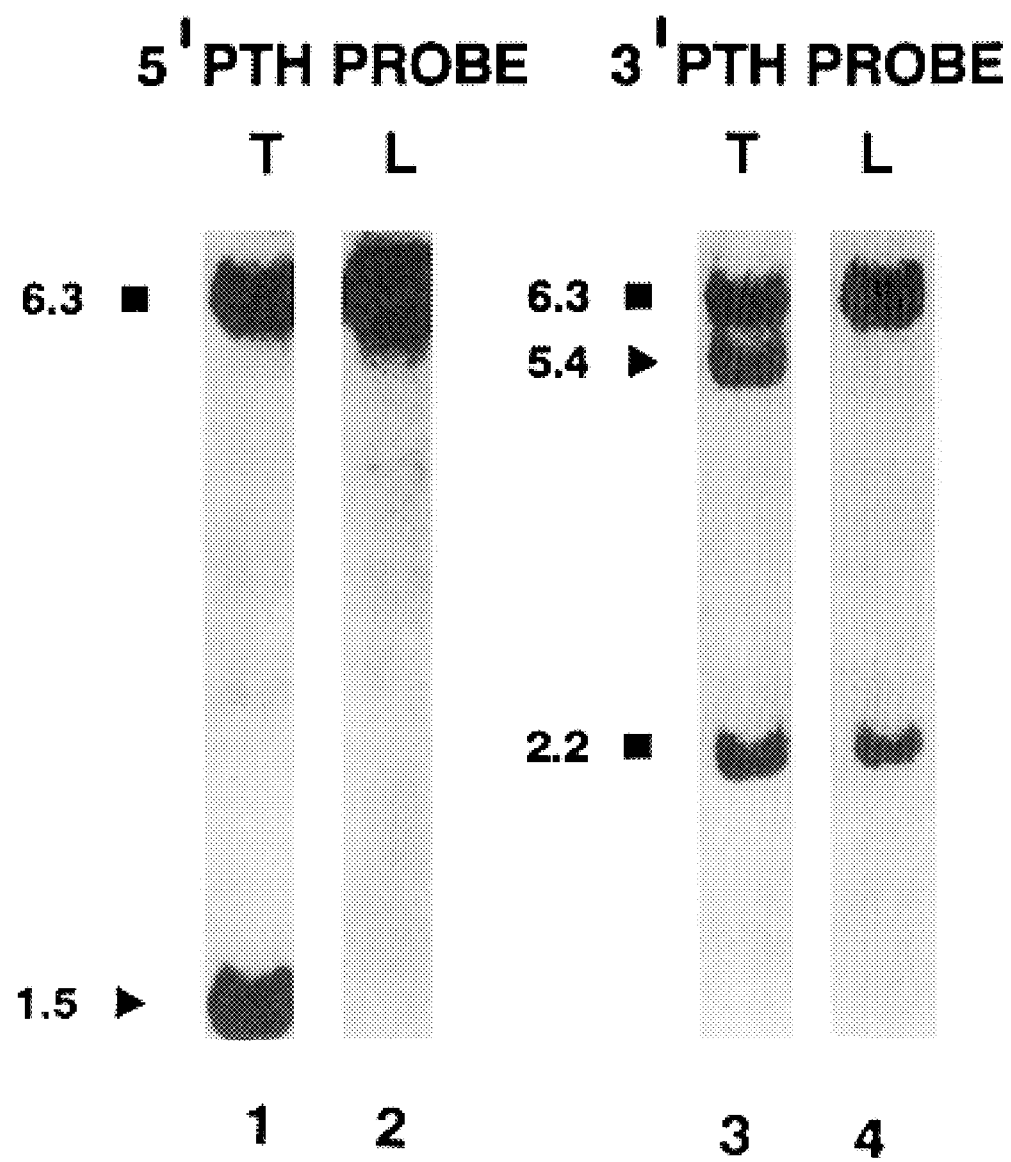

The DNA abnormality in parathyroid tumor M was initially characterized by Southern analysis of MspI digests using probes specific for the 5' and 3' regions in the PTH gene (see below), which revealed a unique, tumor-specific band. FIG. 1 illustrates these Southern blots of tumor M (T) and peripheral blood leukocyte (L) DNA pairs. MspI-digested DNA was probed with the 5' PTH gene probe (lanes 1, 2) and 3' PTH gene probe (lanes 3, 4). Squares indicate the normal gene (6.3 kb); arrows indicate the rearranged allele (1.5 kb in lane 1, 5.4 kb in lane 3). There is an MspI site within the DNA to which the 3' probe hybridizes (see FIG. 2a); therefore, a smaller band (2.2 kb) representing the most 3' section of the normal PTH gene is present in lanes 3 and 4. The intensities of the bands representing the abnormal allele were approximately equal to those representing the normal allele. Thus, in tumor M, as in tumor Y (Arnold et al., 1989), a clonal rearrangement of the PTH gene has occurred: in every tumor cell, one of the two alleles of the PTH gene remains normal but the other is disrupted. FIG. 2(a) illustrates the normal PTH gene, with the positions of its three exons (Vasicek et al., Proc. Natl. Acad. Sci. U.S.A. 80:2127–2131, 1983), the 5' and 3' probes used in mapping and cloning, and the MspI sites indicated. In comparison, FIG. 2(b) shows the two fragments resulting from the rearrangement in tumor M: one consists of the 5' PTH gene sequences plus juxtaposed non-PTH DNA (stippled area), while the other consists of 3' PTH gene sequences plus juxtaposed non-PTH DNA (cross-hatched area). In each fragment, the location of the breakpoint is shown by a diagonal line. The locations of several restriction enzyme sites, determined by Southern blot analysis of tumor DNA, are indicated: EcoRI (R), BamHI (B), HindIII (H), XhoI (X), SstI (S), MspI (M). The locations and sizes of the 1.5 kb and 5.4 kb rearranged MspI fragments, (shown in FIG. 1) are indicated above each fragment. Below each fragment, lines ending in arrow tips depict the 1.5 kb and 16 kb cloned tumor DNA fragments. Analysis with multiple additional restriction enzymes indicated that the gene is separated into two parts, with the breakpoint located in the first intron (FIG. 2b). Consequently, upstream regulatory elements and the first, non-coding exon in the 5' fragment are separated from the coding sequences in the 3' fragment. Each PTH gene fragment remains internally intact (within the limits of sensitivity of restriction mapping), but has become juxtaposed to non-PTH DNA.

To identify the rearranged non-PTH DNA (shaded and cross-hatched areas in FIG. 2b), two DNA fragments containing PTH gene sequences plus breakpoint-adjacent DNA were cloned from tumor M DNA. One was a 16 kb BamHI fragment containing approximately 8 kb of non-PTH gene DNA adjacent to 8 kb of 3' PTH gene sequences (FIG. 2b). Genomic Southern blots of normal DNA probed with subclones spanning most of the 8 kb of non-PTH DNA showed diffuse smears that did not yield to attempts at competition with excess human DNA (Sealy et al., 1985). This indicated that the non-PTH DNA in the 16 kb fragment contained sequences highly repeated in the human genome, and precluded its chromosomal localization.

We also cloned a 1.5 kb EcoRI fragment containing approximately 1 kb of the PTH gene's 5' region plus 500 bp of juxtaposed non-PTH DNA (FIG. 2b). Probing normal human DNA blots with the subcloned 500 bp fragment demonstrated that it contained single-copy DNA; in situ hybridization and analysis of somatic cell hybrids revealed that the 500 bp fragment's normal chromosomal location is 11q13.

Figure 3:
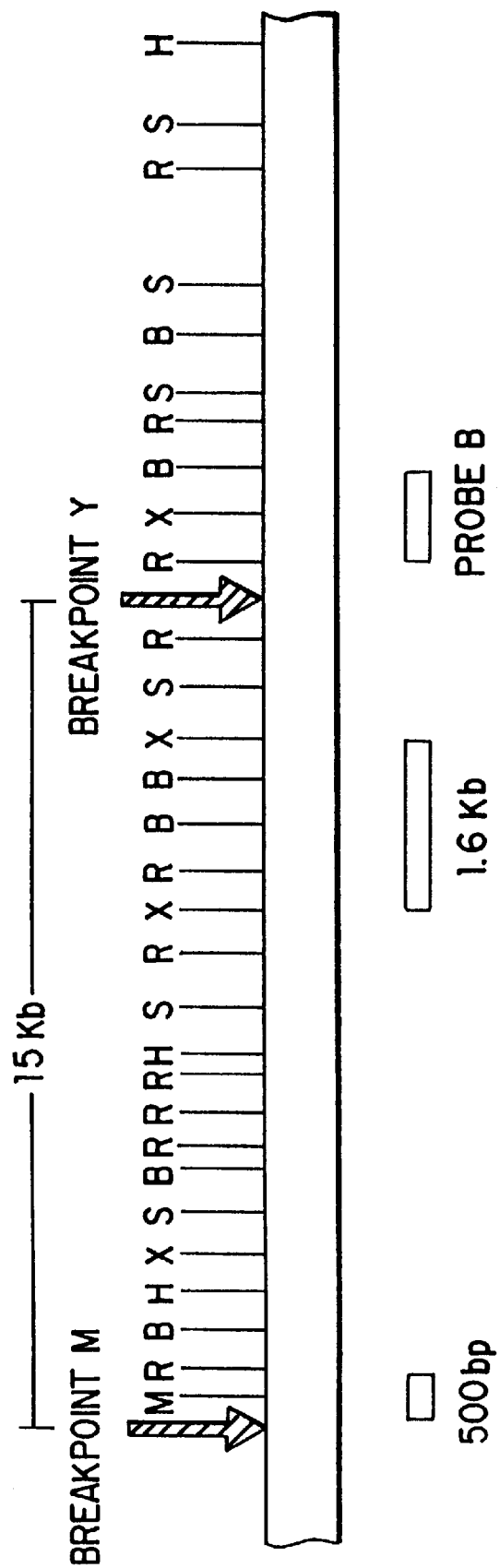
FIG. 3 is diagrammatic representation of the D11S287 region, indicating known restriction sites and the locations of the 500 bp fragment, the 1.6 kb XhoI fragment, and Probe B.

Hybridization of the 500 bp breakpoint-adjacent DNA fragment to an RNA blot of six parathyroid adenomas, including two with PTH gene rearrangements, was negative. To identify transcribed sequences near the breakpoint that could have been affected by the rearrangement, we walked along the chromosome by probing a normal human genomic library with the 500 bp subcloned fragment. We obtained a bacteriophage clone with a 14 kb insert, but Northern blot analyses revealed no hybridization of subclones spanning the entire insert. Mapping of the 14 kb insert showed that the 500 bp fragment was at one end, and demonstrated that the adjacent cloned DNA had a restriction map identical to that of the genomic DNA juxtaposed to tumor M's rearranged 5' PTH gene fragment. (Compare FIGS. 2b and 3). At the other end of the 14 kb insert was a 1.6 kb XhoI fragment (FIG. 3) identical in size to an XhoI fragment 1 kb from tumor Y's D11S287 breakpoint (Arnold et al., 1989). We subcloned these two independent 1.6 kb XhoI fragments (one from the above normal phage clone and one from a tumor Y-derived clone) and used them sequentially to probe blots of normal human genomic DNA digested with 7 restriction enzymes. With every enzyme, the two probes hybridized to precisely comigrating fragments. In addition, restriction maps of the two 1.6 kb fragments themselves were identical for all 6 enzymes used. Thus, the 1.6 kb XhoI fragment linked tumor M's breakpoint-adjacent DNA with that of tumor Y (D11S287), confirming that the 11q13 breakpoints in the two adenomas are both in the D11S287 region, separated by 15 kb. The composite restriction map of the unrearranged D11S287 region is shown in FIG. 3, in which restriction sites for the enzymes HindIII (H), BamHI (B), EcoRI (E), SacI (S), MspI (M) and XhoI (X) are indicated. The locations of the 500 bp fragment, the 1.6 kb XhoI fragment, and probe B are shown. This map is derived from the maps of the phage clones described above and by Arnold et al. (1989), and Southern blots of DNA from tumors M and Y.

Figure 4:
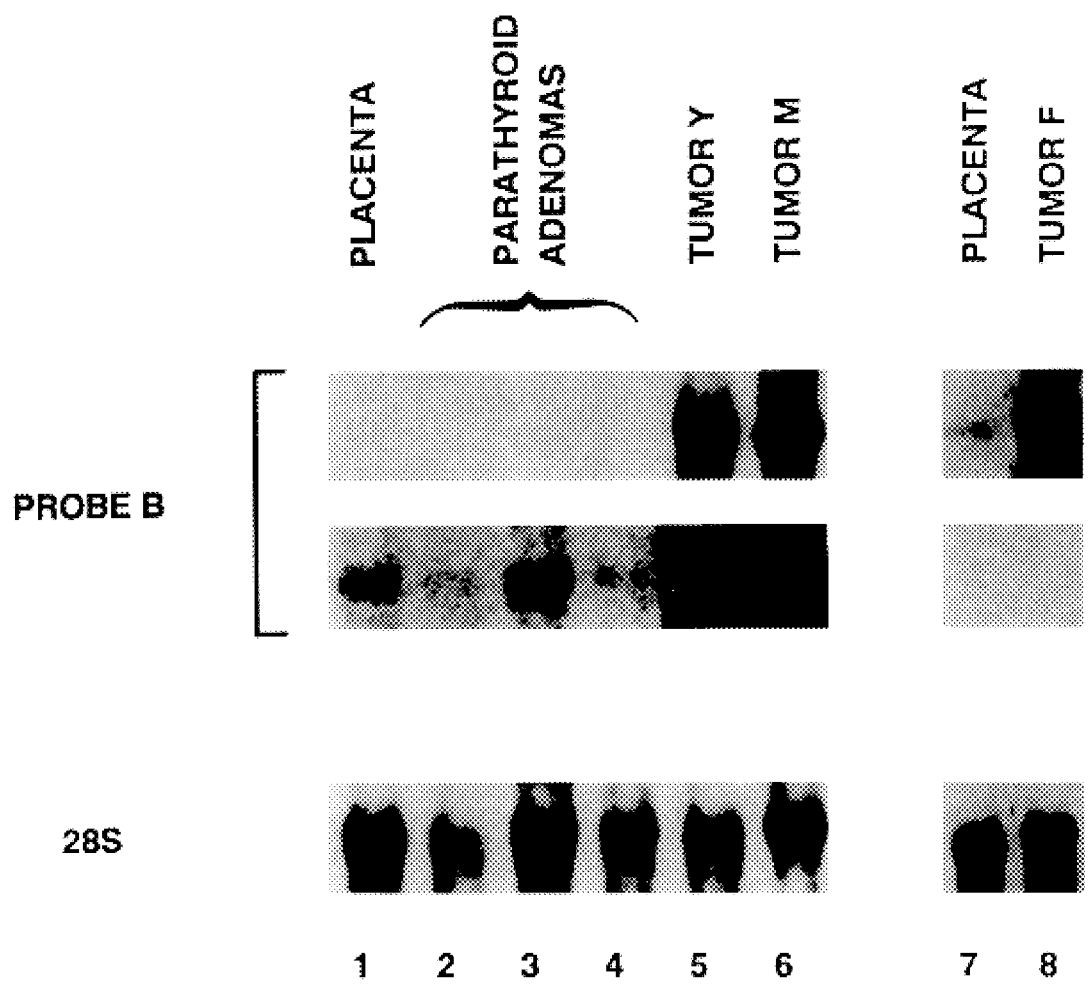
FIG. 4 is a Northern analysis of D11S287 expression in various cell types.

The proximity of the 11q13 breakpoints suggested that the rearrangements could have similar functional consequences. Because none of the DNA between the two tumors' breakpoints is transcribed in parathyroid cells, we looked for transcribed sequences distal to tumor Y's breakpoint. We used fragment B (FIG. 3), a breakpoint-adjacent DNA fragment from tumor Y, to probe a blot containing total RNA from human placenta, several parathyroid adenomas lacking PTH gene rearrangements, and tumors M and Y. We also hybridized probe B to another blot containing total RNA from placenta and from another parathyroid adenoma (tumor F) that was found recently to contain a clonal rearrangement of the PTH and D11S287 loci (Friedman et al., 1990); Southern blotting indicated that tumor F's rearrangement closely resembled tumor Y's. FIG. 4 presents the results of the Northern blots, in which 10 micrograms of total RNA was probed with Probe B (top panels), and with a 28S rRNA probe (bottom panels). Size determination was based on the migration of 28S rRNA. Lanes contain the following samples: lanes 1, 7: placenta; lanes 2, 3, 4: parathyroid adenomas without PTH gene or D11S287 rearrangements; lanes 5, 6, 8: tumors Y, M, and F, respectively; lanes 7 and 8 are a separate Northern filter. The middle panel is a longer exposure of lanes 1–6 in the top panel. In lanes 5 and 8 (tumors Y and F) a faint band was visible, larger than the highly-overexpressed 4.5 kb band, which was not seen in lane 6 (tumor M) (data not shown). Exposure times: top row (probe B): lanes 1–6, 17 h; lanes 7 and 8, 12 h; Middle row (probe B): all lanes, 52 h; Bottom row (28S rRNA): all lanes, 1.5 h. An approximately 4.5 kb transcript (slightly smaller than the 28S rRNA band) was seen in all lanes of FIG. 4. However, the intensity of the 4.5 kb band in tumors M, Y and F was roughly 15-fold greater than that in any of the other specimens. We demonstrated that the 4.5 kb band represents polyadenylated RNA by finding its intensity amplified in poly A+ RNA (data not shown).

Parathyroid adenoma M initially was identified as having an abnormal PTH gene during studies of the monoclonality of parathyroid adenomas (tumor 1 in Arnold et al., N. Eng. J. Med. 318:658–662, 1988). All tumor specimens were frozen in liquid nitrogen shortly after surgical removal. Extraction of high molecular weight DNA, restriction enzyme digestion and Southern blotting were performed as previously described (Arnold et al., N. Eng. J. Med., 309:1593–1599, 1983). Total RNA was isolated by the guanidinium thiocyanate/cesium chloride method, electrophoresed on a denaturing formaldehyde-agarose gel, and transferred to nitrocellulose or nylon filters (Sambrook et al., Molecular Cloning, A Laboratory Manual, 2nd edn. Cold Spring Harbor Laboratory Press, Cold Spring Harbor, N.Y., pp. 7.19–7.22, 7.37–7.39, 11.31–11.32, 1989). Hybridization conditions were similar to those used for Southern filters. Blots were washed at high stringency (0.1×SSC, 65°).

PTH gene fragments used as hybridization probes were the 775 bp BglII fragment (5' PTH probe) and the 2.6 kb SstI-EcoRI fragment (3' PTH probe) from pPTHg108 (Igarashi et al., Mol. Cell. Biol. 6:1830–1833, 1986) (FIG. 2a). The 500 bp fragment and probe B (FIG. 3) were subcloned into pUC-18 from the breakpoint-adjacent DNA of the phage clones containing the rearranged PTH gene fragment plus juxtaposed DNA from tumor M (see above), and tumor Y (Arnold et al., 1989), respectively. The 1.6 kb XhoI fragment from the 14 kb insert cloned from the normal human genomic library was also sub-cloned into pUC-18. The 1.6 kb XhoI fragment from tumor Y was subcloned from a λphage 2001 clone containing the 17 kb HindIII fragment of tumor Y's unrearranged D11S287 allele (Arnold et al., 1989). All the above probes were random-primed and labelled with [$^{32}$P]dATP (Feinberg & Vogelstein, Anal. Biochem. 132:6–13, 1983). The 28S RNA oligonucleotide was end-labelled with [$^{32}$P]dATP (Sambrook et al., 1989) and used to probe the Northern filters to control for the amount of high molecular weight RNA present in each lane.

To clone the rearranged 5' PTH gene fragment (FIG. 2b), an EcoRI library of tumor genomic DNA was constructed using the λZapII vector (Stratagene). This library was screened with the 5' PTH gene probe, and the rearranged allele was distinguished from the normal allele by size, as DNA blots predicted that the rearranged EcoRI fragment would be 1.5 kb in size, and the normal fragment 3.5 kb. One clone containing the rearranged gene was identified in 1×10$^6$ plaques that were screened.

To clone the rearranged 3' PTH gene fragment (FIG. 2b), a BamHI library of tumor genomic DNA was constructed in EMBL-3. Because restriction mapping indicated that both the normal and rearranged 3' PTH BamHI fragments were 16 kb in size, the library was screened with the 3' PTH probe (expected to hybridize to both the normal and rearranged PTH alleles) and then with the 5' PTH probe (expected to hybridize only to the normal allele). One clone containing the rearranged allele was identified in 6.5×10$^3$ plaques screened. As predicted, it contained 8 kb of 3' PTH gene sequences and 8 kb of newly-juxtaposed DNA. Most of this 8 kb was sub-cloned in roughly 2 kb units into pUC-18, and used to probe Southern filters of normal genomic DNA.

Prereassociation was performed by sonicating 1 mg of human placental genomic DNA and incubating it for 10–60 min with 50–100 ng of labelled repeat-containing subcloned DNA. This mix was then hybridized to a Southern filter containing normal human DNA using standard conditions.

The genomic library used to obtain the 14 kb insert was a partial Sau-3a digest of normal human DNA cloned into an EMBL-3 like vector (Clontech).

Chromosomal mapping using human-mouse somatic cell hybrids (Shows et al., Adv. Hum. Genet. 12:341–452, 1982; Shows et al., Somatic Cell Mol. Genet. 10:315–318, 1984); Southern blotting (Naylor et al., J. Exp. Med. 57:1020–1027, 1983); and in situ hybridization (Zabel et al., Cytogenet. Cell Genet. 39:200–205, 1985; Nakai et al., Cytogenet. Cell Genet. 43:215–217, 1986) was performed as previously described.

Figure 5:
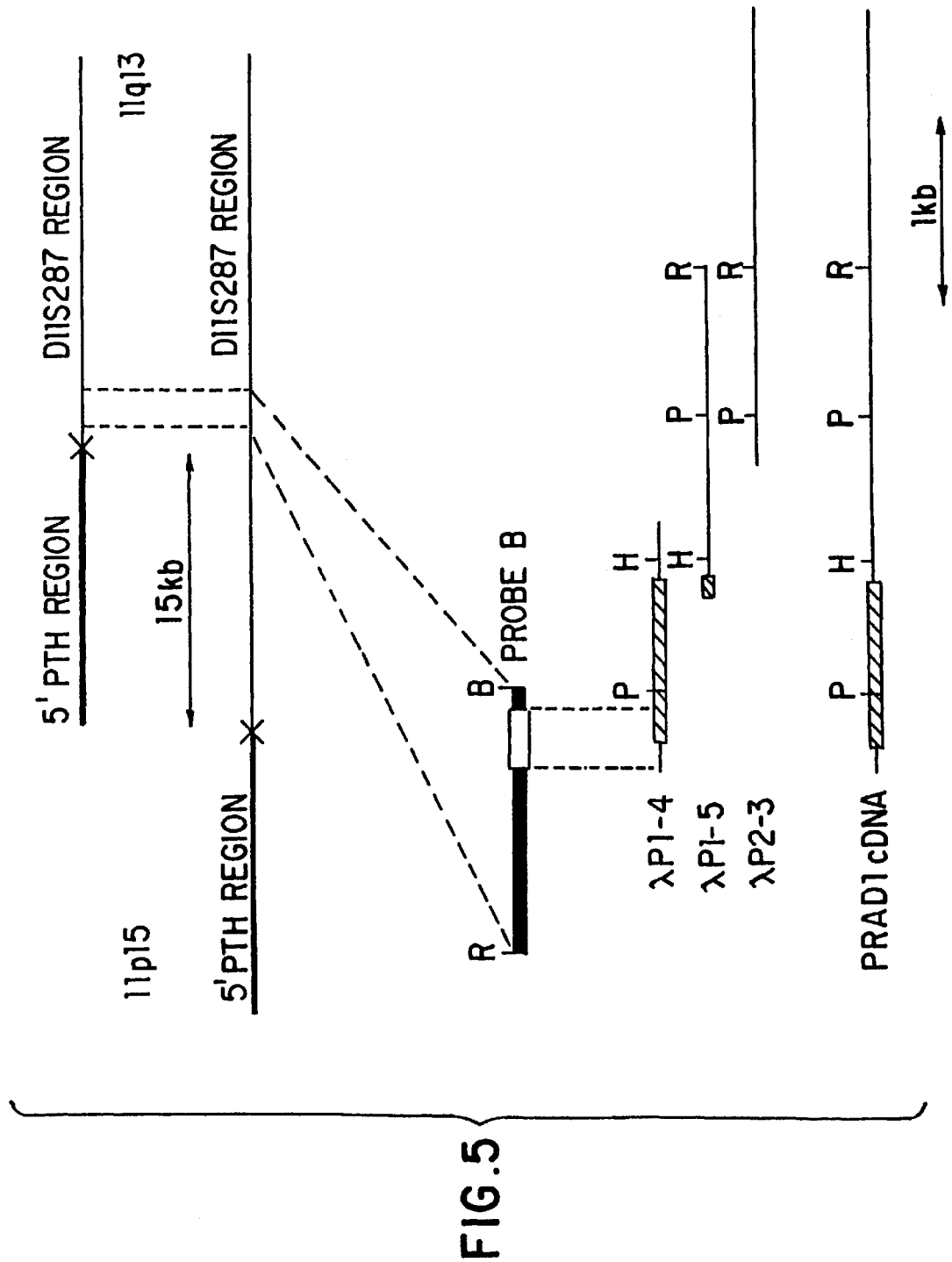

A λgt11 placental cDNA library (Clontech) was screened with radiolabeled Probe B. A clone denominated λP1-4 and another similar phage clone were isolated. Probe B and the insert of λP1-4 were sequenced. The region of genomic and cDNA overlap was followed in Probe B by a GT splice donor sequence in only one orientation, confirming hybridization data which had suggested transcription in the left to right orientation, as shown in FIG. 5. The next probe was made by polymerase chain reaction amplification of the 3' region of the λP1-4 cDNA insert, and used to rescreen the same library. From $5 \times 10^5$ pfu of this library, one of 16 positive clones, λP1-5, had an insert extending further downstream. The PstI/EcoRI fragment of λP1-5 was then used to rescreen the library, and 12 similar clones, the longest of which was λP2-3, were obtained. The sequence of the insert of λP2-3 revealed polyadenylation signals and a polyA stretch of 16 nucleotides in an appropriate position, consistent with the expected orientation. Standard methods for library screening and probe labeling were used (Davis et al., Basic Methods in Molecular Biology (Elsevier, New York, Amsterdam, London, 1986). These clones are illustrated in FIG. 5, together with a schematic representation of PTH/D11S287 rearrangements in two parathyroid adenomas. The 5' PTH region (11p15, thick lines) was juxtaposed to the D11S287 region (11q13, thin lines) in each of these adenomas. The breakpoints in the D11S287 region are 15 kb apart. Genomic Probe B is shown as a darkened box, whose open area represents the first exon of PRAD1. Also shown are restriction maps of the inserts of representative overlapping PRAD1 cDNA clones, λP1-4, λP1-5, and λP2-3; and the deduced restriction map of the PRAD1 cDNA. The coding region is shown as a crosshatched box. Scale of 1 kb is shown as arrows. Symbols used for restriction sites are: B, BamHI; E, EcoRI; H, HindIII; P, PstI.

The inserts of the clones λP1-4, λP1-5, and λP2-3 shown in FIG. 5, and of other independent clones, were subcloned into pGEM7Zf(+) (Promega). Sequences were obtained using the double-stranded DNA sequencing technique (dideoxy method) with modified T7 DNa polymerase (Sequenase; U.S. Biochemical Corporation), as described by the manufacturer. Several oligonucleotides were synthesized as internal primers to facilitate sequencing. The coding region was sequenced in both orientations and in at least two independent clones. Set forth in FIG. 6 are the nucleotide sequence and predicted amino acid sequence of human PRAD1 cDNA (SEQ ID NO:1). Nucleotide numbers are on the right. Nucleotide 3495, shown as W, indicates A or T because the sequences of two independent clones did not agree. Nucleotide 4017 is shown as R, meaning A or G, for the same reason.

FIG. 7 illustrates sequence homology between the "cyclin box" region of the predicted PRAD1 protein (prad1) (SEQ ID NO.4) and that of A-type cyclins (human (SEQ ID NO.3) and clam cyclin A (SEQ ID NO.5)) (Swenson et al., Cell 47:861–870, 1986, and Wang et al., Nature 343:555–557, 1990); B-type cyclins (human cyclin B (SEQ ID NO.6) and S. pombe cdc13 (SEQ ID NO.7)) (Pines et al., Cell 58:833–846, 1989; and Booher et al., EMBO J. 7:2321–2327, 1988), and one S. cerevisiae G1 cyclin (cln3) (SEQ ID NO.8) (Nash et al., EMBO J. 7:4335–4346, 1988; Cross et al., Mol. Cell. Biol. 8:4675–4684, 1988). Clam cyclin A (SEQ ID NO.5) and S. pombe cdc13 (SEQ ID NO.7) homologies with prad1 are representative of those found in their families; cln3 (SEQ ID NO.8) alignes with prad1 more closely than does cln1 or 2. Identical amino acids are shown as |. Conservative substitutions are shown as *. Alignment was made with the assistance of the BESTFIT program (Devereux et al., Nucl. Acids Res. 12:387–395, 1984) and conservative amino acids are grouped as follows: D, E, N, Q; H, K, R; A, G, P, S, T; I, L, M, V; F, W, Y. Amino acid numbers are on the right in this Figure.

RNAs were prepared for Northern blot analysis from the indicated tissues by standard procedures (Davis et al., 1986). 10 μg total RNA was loaded and separated on an agarose-formaldehyde gel, blotted onto nitrocellulose, and hybridized with Probe B or the 28S rRNA oligonucleotide. The filters were washed at high stringency (0.1×SSC, 60° C.) and autoradiographed. FIG. 8 illustrates a Northern blot analysis of total RNA from human thyroid (lane 1), human placenta (lane 2), bovine parathyroid (lane 3), bovine thyroid (lane 4), bovine lymph node (lane 5), bovine skeletal muscle (lane 6), murine heart (lane 7), and murine liver (lane 8). PRAD1 mRNA (shown in the upper panel) is approximately 4.5 kb in size, slightly smaller than the 28S rRNA; 28S rRNA hybridization is shown in the lower panel. FIG. 9(a) shows a Northern blot analysis of total RNA from HeLa S3 cells after release from G1/S block. Hela S3 cells (American Type Culture Collection), maintained in Dulbecco Modified Eagle Medium (DMEM, GIBCO) with 7% fetal bovine serum (FBS), were synchronized at the G1/S boundary by sequential thymidine-aphidicolin treatment (Heintz, et al., Mol. Cell. Biol. 3:539–550, 1983) with a slight modification. Log-phase cells were incubated in complete medium (DMEM with 7% FBS, penicillin G, and streptomycin) with addition of 2 mM thymidine (Sigma) for 12 h. After release from thymidine block by 3 washes with PBS, the cells were incubated for 10 h with 24 μM deoxycytidine (Sigma) and 24 μM thymidine, recovered by trypsinization, counted, and aliquoted equally ($5.0 \times 10^4$ cells/cm$^2$). Incubation with 5 μg/ml aphidicolin (Sigma) for 14 h was followed by release from G1/S block with 4 DMEM washes and incubation in complete medium. [$^3$H]Thymidine (NEN) was added to an aliquot 15 min before each indicated time point; a 30 min incubation and harvesting for trichloroacetic acid (TCA) precipitation followed. RNAs from parallel aliquots were extracted (Chomczynski et al., Anal. Biochem. 162:156–159, 1987) at the indicated times; time zero was just before release from aphidicolin. RNAs (5 μg per lane) were blotted onto nitrocellulose and sequentially hybridized with the PRAD1 λp1-4 cDNA insert, human H4 histone pF0108X (Pauli et al., Science 236:1308–1311, 1987), and a 28S rRNA oligonucleotide as described above. Human PRAD1 mRNA is shown in the upper panel of FIG. 9(a); H4 histone mRNA in the middle panel shows the pattern expected in well-synchronized cells (Heintz et al., 1983); and 28S rRNA is shown in the lower panel as a control for RNA loading. In FIG. 9(b) are compared the relative amounts of human PRAD1 mRNA (-●-), H4 histone mRNA (-○-), and [$^3$H]thymidine incorporation (-□-) of HeLa S3 cells after release from G1/S block. The signals of the blot shown in FIG. 9(a) were measured by densitometry and normalized to the 28S rRNA to produce the graph of FIG. 9(b).

Clam embryo interphase cell lysates lacking endogenous cyclins were prepared by adding 100 μM emetine during first mitosis, as described previously (Luca et al., J. Cell Biol. 109:1895–1909, 1989), followed by homogenization and centrifugation at 150,000×g. Aliquots of the supernatant were frozen in liquid nitrogen. [$^{35}$S]methionine-labeled prad1 was produced in a reticulocyte lysate in vitro translation system (Promega) according to manufacturer's instructions, by using a plasmid (denominated pP1-8) containing the λP1-4 insert in pGEM7Zf(+) (Promega). To produce prad1 in *E. coli*, pT4R-1 was constructed by insertion of the λP1-4 insert into the NcoI and BamHI sites of pET-3d (Studier et al., Meth. Enzym. 108:60–89, 1990). BL21(DE3) cells were transformed with pT4R-1, cultured, and treated with 0.4 mM isopropylthio-beta-galactosidase (IPTG) for 3 h to induce prad1 expression. The induced product was purified from cell culture as inclusion bodies (Gardella et al., J. Biol. Chem 265:15854–15859, 1990). On SDS-polyacrylamide gels, the apparent sizes of the in vitro translation product and the bacterially-expressed product were the same ($M_r$ 35 kD). Rabbit anti-prad1 antisera were raised against a synthetic peptide corresponding to amino acids 9–37 of prad1. Antisera were assayed by immunoprecipitation of the in vitro translation product. Antisera specificity was shown by comparison with normal rabbit serum and by successful competition with the (9–37) peptide (data not shown).

Thawed clam embryo lysate (16.5 μl) and bacterially-expressed prad1 (5.5 μl) were mixed and incubated at 18° C. for 30 min before transfer to 4° C., dilution with 4 volumes of buffer A (50 mM Tris pH 7.4, 150 mM NaCl, 5mM EDTA, 5mM EGTA, 1 mM ammonium molybdate) and addition of p13$^{suc1}$- or protein A-Sepharose, followed by mixing for 1 h. Beads were then pelleted and washed in buffer A+0.5% Tween-20; in buffer B (50 mM Tris pH 7.4, 1.0 M NaCl, 5 mM EDTA, 5 mM EGTA, 1 mM molybdate, 0.5% Tween-20); and finally in buffer A without Tween-20, all at 4° C. Washed beads were boiled in SDS sample buffer for 3 min and the supernatant split into three samples for electrophoresis. Gels were silver stained or blotted onto nitrocellulose filters and reacted with rabbit antibodies generated against bacterially-expressed, full-length *S. pombe* cdc2 protein or prad1 peptide as above. Antibody binding was visualized by alkaline phosphatase-linked secondary antibodies, according to the manufacturer's directions (Promega). FIG. 10 demonstrates that prad1 protein added to clam embryo cell lysates binds to p13$^{suc1}$-Sepharose beads and activates histone H1 kinase activity. Bacterially expressed prad1 was incubated with a clam embryo interphase lysate lacking endogenous cyclins A and B. The lysates were then mixed with p13$^{suc1}$- or protein A-Sepharose beads. The bound material was eluted, electrophoresed and either silver stained (a) or immunoblotted with anti-prad1 antiserum (b) or anti-cdc2 antiserum (c). Lane M shows molecular weight markers (from top to bottom) of 116, 94, 68, 56, 40, and 31 kD. Lane 1 shows whole clam embryo interphase lysate plus 18 ng prad1 protein. Lanes 2, 3, 4, 5, and 6 represent clam embryo lysate to which 0, 18, 45, 225, or 18 ng of prad1, respectively, were added; these mixes were then assayed for material binding to p13$^{suc1}$-Sepharose (lanes 2–5) or protein A-Sepharose (lane 6) beads. Lane 7 shows bacterially-expressed prad1. Arrows indicate the positions of prad1 and cdc2 marker proteins.

Equal volumes of clam embryo interphase lysate and reticulocyte lysate containing [$^{32}$P]-labeled kinase products were then examined by SDS-PAGE, followed by autoradiography. Synthetic clam cyclins A and B (Westendorf et al., J. Cell Biol. 108:1431–1444; Swenson et al., Cell 47:861–870, 1986) and prad1 mRNAs were transcribed and translated as described above. Translation product (3 μl) and clam embryo lysate (3 μl) were mixed. Samples were frozen immediately in liquid nitrogen. The remainder was incubated for 30 min at 18° C. and then frozen. Samples were diluted with 1 volume of ice-cold buffer A, thawed on ice, and mixed with an equal volume of kinase mix (40 mM Hepes pH 7.3, 20 mM $MgCl_2$, 10 mM EGTA, 0.2 mg/ml histone H1, 10 μM cAMP-dependent kinase inhibitor (Sigma), 0.5 mCi/ml [γ-$^{32}$P]ATP and incubated at 23° C. for 10 min. Double-strength SDS sample buffer was then added and the entire mix was analyzed by SDS-PAGE followed by autoradiography, as shown in FIG. 10(*d*).

What is claimed is:

1. An isolated DNA molecule comprising a sequence encoding prad1, a cyclin which induces kinase activity in a clam embryo interphase cell lysate, wherein said DNA molecule hybridizes under stringent hybridization conditions to a single-stranded probe consisting of a segment of 40 nucleotides of human PRAD1 cDNA (SEQ ID NO:1).

2. The DNA molecule of claim 1, wherein said prad1 has the same amino acid sequence as the polypeptide encoded by SEQ ID NO:1.

3. An essentially purified vector, said vector comprising an isolated DNA molecule having a DNA sequence encoding prad1, a cyclin which induces kinase activity in a clam embryo interphase cell lysate, wherein said DNA molecule hybridizes under stringent hybridization conditions to a single-stranded probe consisting of a segment of 40 nucleotides of human PRAD1 cDNA (SEQ ID NO:1).

4. The vector of claim 3, wherein said DNA sequence encoding prad1 is under the transcriptional control of a heterologous promoter.

5. A cultured cell comprising an isolated DNA molecule encoding prad1, a cyclin which induces kinase activity in a clam embryo interphase cell lysate, wherein said DNA molecule hybridizes under stringent hybridization conditions to a single-stranded probe consisting of a segment of 40 nucleotides of human PRAD1 cDNA (SEQ ID NO:1).

6. The cell of claim 5, wherein said isolated DNA molecule is integrated into the genome of said cell.

7. The cell of claim 6, wherein said cell is a eukaryotic cell.

8. The cell of claim 5, wherein said cell expresses said prad1 from said isolated DNA molecule, wherein said prad1 is encoded by a DNA sequence under the transcriptional control of a promoter.

9. A method for using the cell of claim 5, which method comprises
culturing said cell in a medium under conditions suitable for expression; and
recovering prad1 from said cell or said medium.

10. The method of claim 9, wherein said prad1 has the same amino acid sequence as the polypeptide encoded by SEQ ID NO:1.

11. The cell of claim 5, wherein said prad1 has the same amino acid sequence as the polypeptide encoded by SEQ ID NO:1.

12. A population of cultured cells, each of which comprises an isolated DNA molecule encoding prad1, a cyclin which induces kinase activity in a clam embryo interphase cell lysate, wherein said DNA molecule hybridizes under stringent hybridization conditions to a single-stranded probe consisting of a segment of 40 nucleotides of human PRAD1 cDNA (SEQ ID NO:1).

13. The population of cells of claim 12, wherein each of said cells is a eukaryotic cell.

14. The population of cells of claims 12, wherein each of said cells is a prokaryotic cell.

15. The population of cells of claim 12, wherein said prad1 has the same amino acid sequence as the polypeptide encoded by SEQ ID NO:1.

16. A method for using an isolated nucleic acid encoding prad1, said prad1 being a cyclin which induces kinase activity in a clam embryo interphase cell lysate, which method comprises
introducing said isolated nucleic acid encoding prad1 into a reticulocyte lysate in vitro expression system;
incubating said expression system to produce said prad1; and recovering said prad1 from said expression system, wherein said isolated nucleic acid hybridizes under stringent hybridization conditions to a single-stranded probe consisting of a segment of at least 40 nucleotides of human PRAD1 cDNA (SEQ ID NO:1).

17. The method of claim 16, wherein said prad1 has the same amino acid sequence as the polypeptide encoded by SEQ ID NO:1.

18. An isolated, single-stranded DNA molecule comprising a segment of a PRAD1, each of said PRAD1 and said segment being a DNA molecule which hybridizes under stringent hybridization conditions to the prad1-encoding cDNA sequence of SEQ ID NO:1, or the complement thereof, said segment being at least 18 nucleotides in length.

19. The single-stranded DNA molecule of claim 18, wherein said PRAD1 is a genomic PRAD1.

20. The single-stranded DNA molecule of claim 18, wherein said PRAD1 is a PRAD1 cDNA.

21. The single-stranded DNA molecule of claim 18, wherein said DNA molecule is radioactively labelled.

22. The single-stranded DNA molecule of claim 18, wherein said DNA molecule is antisense.

23. The single-stranded DNA molecule of claim 18, wherein said PRAD1 is human PRAD1.

24. The single-stranded DNA of claim 23, wherein said PRAD1 is human PRAD1 cDNA (SEQ ID NO:1).

25. An essentially purified RNA molecule comprising a sequence encoding prad1, a cyclin which induces kinase activity in a clam embryo interphase cell lysate, wherein said RNA molecule hybridizes under stringent hybridization conditions to a single-stranded probe consisting of a segment of at least 40 nucleotides of human PRAD1 cDNA (SEQ ID NO:1).

26. The RNA molecule of claim 25, wherein said prad1 is human prad1.

27. An isolated DNA molecule comprising a sequence encoding prad1, a cyclin which induces kinase activity in a clam embryo interphase lysate, wherein said sequence encoding prad1 consists of the sequence of SEQ ID NO:1.

28. An isolated, double-stranded DNA molecule comprising a segment of a PRAD1, said PRAD1 being a DNA molecule which hybridizes under stringent hybridization at least 18 nucleotides in length which hybridizes under stringent hybridization conditions to the prad1-encoding cDNA sequence of SEQ ID NO:1 or the complement thereof.

* * * * *

UNITED STATES PATENT AND TRADEMARK OFFICE
CERTIFICATE OF CORRECTION

PATENT NO.    : 6,110,700
DATED         : August 29, 2000
INVENTOR(S)   : Arnold It is certified that error appears in the above-identified patent and that said Letters Patent is hereby corrected as shown below:

<u>Title page, Item [54] and Column 1, line 1,</u>
Please change the title of the invention by deleting "PRAD1 CYCLIN AND ITS CDNA" and inserting therefor -- PRAD1 CYCLIN (CYCLIN D1) AND ITS CDNA --.

Signed and Sealed this

Second Day of September, 2003

JAMES E. ROGAN
*Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 4244 base pairs
      (B) TYPE: nucleic acid
      (C) STRANDEDNESS: double
      (D) TOPOLOGY: both (ii) MOLECULE TYPE: cDNA (ix) FEATURE:
      (A) NAME/KEY: CDS
      (B) LOCATION: 148..1032

(xi) SEQUENCE DESCRIPTION: SEQ ID NO:1:

```
GGCGCAGTAG CAGCGAGCAG CAGAGTCCGC ACGCTCCGGC GAGGGGCAGA AGAGCGCGAG        60

GGAGCGCGGG GCAGCAGAAG CGAGAGCCGA GCGCGGACCC AGCCAGGACC CACAGCCCTC       120
```

-continued

| | | | | | | | | | | | | | | | | |
|---|---|---|---|---|---|---|---|---|---|---|---|---|---|---|---|---|
| CCCAGCTGCC | CAGGAAGAGC | CCCAGCC | ATG | GAA | CAC | CAG | CTC | CTG | TGC | TGC | | | | | | 171 |
| | | | Met | Glu | His | Gln | Leu | Leu | Cys | Cys | | | | | | |
| | | | 1 | | | | 5 | | | | | | | | | |
| GAA | GTG | GAA | ACC | ATC | CGC | CGC | GCG | TAC | CCC | GAT | GCC | AAC | CTC | CTC | AAC | 219 |
| Glu | Val | Glu | Thr | Ile | Arg | Arg | Ala | Tyr | Pro | Asp | Ala | Asn | Leu | Leu | Asn | |
| | 10 | | | | 15 | | | | 20 | | | | | | | |
| GAC | CGG | GTG | CTG | CGG | GCC | ATG | CTG | AAG | GCG | GAG | GAG | ACC | TGC | GCG | CCC | 267 |
| Asp | Arg | Val | Leu | Arg | Ala | Met | Leu | Lys | Ala | Glu | Glu | Thr | Cys | Ala | Pro | |
| 25 | | | | 30 | | | | 35 | | | | | 40 | | | |
| TCG | GTG | TCC | TAC | TTC | AAA | TGT | GTG | CAG | AAG | GAG | GTC | CTG | CCG | TCC | ATG | 315 |
| Ser | Val | Ser | Tyr | Phe | Lys | Cys | Val | Gln | Lys | Glu | Val | Leu | Pro | Ser | Met | |
| | | | 45 | | | | 50 | | | | | 55 | | | | |
| CGG | AAG | ATC | GTC | GCC | ACC | TGG | ATG | CTG | GAG | GTC | TGC | GAG | GAA | CAG | AAG | 363 |
| Arg | Lys | Ile | Val | Ala | Thr | Trp | Met | Leu | Glu | Val | Cys | Glu | Glu | Gln | Lys | |
| | | 60 | | | | 65 | | | | | 70 | | | | | |
| TGC | GAG | GAG | GAG | GTC | TTC | CCG | CTG | GCC | ATG | AAC | TAC | CTG | GAC | CGC | TTC | 411 |
| Cys | Glu | Glu | Glu | Val | Phe | Pro | Leu | Ala | Met | Asn | Tyr | Leu | Asp | Arg | Phe | |
| | | 75 | | | | 80 | | | | 85 | | | | | | |
| CTG | TCG | CTG | GAG | CCC | GTG | AAA | AAG | AGC | CGC | CTG | CAG | CTG | CTG | GGG | GCC | 459 |
| Leu | Ser | Leu | Glu | Pro | Val | Lys | Lys | Ser | Arg | Leu | Gln | Leu | Leu | Gly | Ala | |
| | 90 | | | | 95 | | | | 100 | | | | | | | |
| ACT | TGC | ATG | TTC | GTG | GCC | TCT | AAG | ATG | AAG | GAG | ACC | ATC | CCC | CTG | ACG | 507 |
| Thr | Cys | Met | Phe | Val | Ala | Ser | Lys | Met | Lys | Glu | Thr | Ile | Pro | Leu | Thr | |
| 105 | | | | 110 | | | | 115 | | | | | 120 | | | |
| GCC | GAG | AAG | CTG | TGC | ATC | TAC | ACC | GAC | AAC | TCC | ATC | CGG | CCC | GAG | GAG | 555 |
| Ala | Glu | Lys | Leu | Cys | Ile | Tyr | Thr | Asp | Asn | Ser | Ile | Arg | Pro | Glu | Glu | |
| | | | 125 | | | | 130 | | | | | 135 | | | | |
| CTG | CTG | CAA | ATG | GAG | CTG | CTC | CTG | GTG | AAC | AAG | CTC | AAG | TGG | AAC | CTG | 603 |
| Leu | Leu | Gln | Met | Glu | Leu | Leu | Leu | Val | Asn | Lys | Leu | Lys | Trp | Asn | Leu | |
| | | | 140 | | | | 145 | | | | | 150 | | | | |
| GCC | GCA | ATG | ACC | CCG | CAC | GAT | TTC | ATT | GAA | CAC | TTC | CTC | TCC | AAA | ATG | 651 |
| Ala | Ala | Met | Thr | Pro | His | Asp | Phe | Ile | Glu | His | Phe | Leu | Ser | Lys | Met | |
| | | 155 | | | | 160 | | | | 165 | | | | | | |
| CCA | GAG | GCG | GAG | GAG | AAC | AAA | CAG | ATC | ATC | CGC | AAA | CAC | GCG | CAG | ACC | 699 |
| Pro | Glu | Ala | Glu | Glu | Asn | Lys | Gln | Ile | Ile | Arg | Lys | His | Ala | Gln | Thr | |
| | 170 | | | | 175 | | | | 180 | | | | | | | |
| TTC | GTT | GCC | CTC | TGT | GCC | ACA | GAT | GTG | AAG | TTC | ATT | TCC | AAT | CCG | CCC | 747 |
| Phe | Val | Ala | Leu | Cys | Ala | Thr | Asp | Val | Lys | Phe | Ile | Ser | Asn | Pro | Pro | |
| 185 | | | | 190 | | | | 195 | | | | | 200 | | | |
| TCC | ATG | GTG | GCA | GCG | GGG | AGC | GTG | GTG | GCC | GCA | GTG | CAA | GGC | CTG | AAC | 795 |
| Ser | Met | Val | Ala | Ala | Gly | Ser | Val | Val | Ala | Ala | Val | Gln | Gly | Leu | Asn | |
| | | | 205 | | | | 210 | | | | | 215 | | | | |
| CTG | AGG | AGC | CCC | AAC | AAC | TTC | CTG | TCC | TAC | TAC | CGC | CTC | ACA | CGC | TTC | 843 |
| Leu | Arg | Ser | Pro | Asn | Asn | Phe | Leu | Ser | Tyr | Tyr | Arg | Leu | Thr | Arg | Phe | |
| | | | 220 | | | | 225 | | | | | 230 | | | | |
| CTC | TCC | AGA | GTG | ATC | AAG | TGT | GAC | CCA | GAC | TGC | CTC | CGG | GCC | TGC | CAG | 891 |
| Leu | Ser | Arg | Val | Ile | Lys | Cys | Asp | Pro | Asp | Cys | Leu | Arg | Ala | Cys | Gln | |
| | | 235 | | | | 240 | | | | 245 | | | | | | |
| GAG | CAG | ATC | GAA | GCC | CTG | CTG | GAG | TCA | AGC | CTG | CGC | CAG | GCC | CAG | CAG | 939 |
| Glu | Gln | Ile | Glu | Ala | Leu | Leu | Glu | Ser | Ser | Leu | Arg | Gln | Ala | Gln | Gln | |
| | 250 | | | | 255 | | | | 260 | | | | | | | |
| AAC | ATG | GAC | CCC | AAG | GCC | GCC | GAG | GAG | GAG | GAA | GAG | GAG | GAG | GAG | GAG | 987 |
| Asn | Met | Asp | Pro | Lys | Ala | Ala | Glu | Glu | Glu | Glu | Glu | Glu | Glu | Glu | Glu | |
| 265 | | | | 270 | | | | 275 | | | | | 280 | | | |
| GTG | GAC | CTG | GCT | TGC | ACA | CCC | ACC | GAC | GTG | CGG | GAC | GTG | GAC | ATC | | 1032 |
| Val | Asp | Leu | Ala | Cys | Thr | Pro | Thr | Asp | Val | Arg | Asp | Val | Asp | Ile | | |
| | | | 285 | | | | 290 | | | | | 295 | | | | |
| TGAGGGCGCC | AGGCAGGCGG | GCGCCACCGC | CACCCGCAGC | GAGGGCGGAG | CCGGCCCCAG | | | | | | | | | | | 1092 |
| GTGCTCCACT | GACAGTCCCT | CCTCTCCGGA | GCATTTTGAT | ACCAGAAGGG | AAAGCTTCAT | | | | | | | | | | | 1152 |

-continued

```
TCTCCTTGTT GTTGGTTGTT TTTTCCTTTG CTCTTTCCCC CTTCCATCTC TGACTTAAGC   1212

AAAAGAAAAA GATTACCCAA AAACTGTCTT TAAAAGAGAG AGAGAGAAAA AAAAAATAGT   1272

ATTTGCATAA CCCTGAGCGG TGGGGGAGGA GGGTTGTGCT ACAGATGATA GAGGATTTTA   1332

TACCCCAATA ATCAACTCGT TTTTATATTA ATGTACTTGT TTCTCTGTTG TAAGAATAGG   1392

CATTAACACA AAGGAGGCGT CTCGGGAGAG GATTAGGTTC CATCCTTTAC GTGTTTAAAA   1452

AAAAGCATAA AAACATTTTA AAAACATAGA AAAATTCAGC AAACCATTTT TAAAGTAGAA   1512

GAGGGTTTTA GGTAGAAAAA CATATTCTTG TGCTTTTCCT GATAAAGCAC AGCTGTAGTG   1572

GGGTTCTAGG CATCTCTGTA CTTTGCTTGC TCATATGCAT GTAGTCACTT TATAAGTCAT   1632

TGTATGTTAT TATATTCCGT AGGTAGATGT GTAACCTCTT CACCTTATTC ATGGCTGAAG   1692

TCACCTCTTG GTTACAGTAG CGTAGCGTGG CCGTGTGCAT GTCCTTTGCG CCTGTGACCA   1752

CCACCCCAAC AAACCATCCA GTGACAAACC ATCCAGTGGA GGTTTGTCGG GCACCAGCCA   1812

GCGTAGCAGG GTCGGGAAAG GCCACCTGTC CCACTCCTAC GATACGCTAC TATAAAGAGA   1872

AGACGAAATA GTGACATAAT ATATTCTATT TTTATACTCT TCCTATTTTT GTAGTGACCT   1932

GTTTATGAGA TGCTGGTTTT CTACCCAACG GCCCTGCAGC CAGCTCACGT CCAGGTTCAA   1992

CCCACAGCTA CTTGGTTTGT GTTCTTCTTC ATATTCTAAA ACCATTCCAT TTCCAAGCAC   2052

TTTCAGTCCA ATAGGTGTAG GAAATAGCGC TGTTTTTGTT GTGTGTGCAG GGAGGGCAGT   2112

TTTCTAATGG AATGGTTTGG GAATATCCAT GTACTTGTTT GCAAGCAGGA CTTTGAGGCA   2172

AGTGTGGGCC ACTGTGGTGG CAGTGGAGGT GGGGTGTTTG GGAGGCTGCG TGCCAGTCAA   2232

GAAGAAAAAG GTTTGCATTC TCACATTGCC AGGATGATAA GTTCCTTTCC TTTTCTTTAA   2292

AGAAGTTGAA GTTTAGGAAT CCTTTGGTGC CAACTGGTGT TTGAAAGTAG GGACCTCAGA   2352

GGTTTACCTA GAGAACAGGT GGTTTTTAAG GGTTATCTTA GATGTTTCAC ACCGGAAGGT   2412

TTTTAAACAC TAAAATATAT AATTTATAGT TAAGGCTAAA AAGTATATTT ATTGCAGAGG   2472

ATGTTCATAA GGCCAGTATG ATTTATAAAT GCAATCTCCC CTTGATTTAA ACACACAGAT   2532

ACACACACAC ACACACACAC ACACACAAAC CTTCTGCCTT TGATGTTACA GATTTAATAC   2592

AGTTTATTTT TAAAGATAGA TCCTTTTATA GGTGAGAAAA AAACAATCTG AAGAAAAAA   2652

ACCACACAAA GACATTGATT CAGCCTGTTT GGCGTTTCCC AGAGTCATCT GATTGGACAG   2712

GCATGGGTGC AAGGAAAATT AGGGTACTCA ACCTAAGTTC GGTTCCGATG AATTCTTATC   2772

CCCTGCCCCT TCCTTTAAAA AACTTAGTGA CAAAATAGAC AATTTGCACA TCTTGGCTAT   2832

GTAATTCTTG TAATTTTTAT TTAGGAAGTG TTGAAGGGAG GTGGCAAGAG TGTGGAGGCT   2892

GACGTGTGAG GGAGGACAGG CGGGAGGAGG TGTGAGGAGG AGGCTCCCGA GGGGAAGGGG   2952

CGGTGCCCAC ACCGGGGACA GGCCGCAGCT CCATTTTCTT ATTGCGCTGC TACCGTTGAC   3012

TTCCAGGCAC GGTTTGGAAA TATTCACATC GCTTCTGTGT ATCTCTTTCA CATTGTTTGC   3072

TGCTATTGGA GGATCAGTTT TTTGTTTTAC AATGTCATAT ACTGCCATGT ACTAGTTTTA   3132

GTTTTCTCTT AGAACATTGT ATTACAGATG CCTTTTTTGT AGTTTTTTTT TTTTTATGT   3192

GATCAATTTT GACTTAATGT GATTACTGCT CTATTCCAAA AAGGTTGCTG TTTCACAATA   3252

CCTCATGCTT CACTTAGCCA TGGTGGACCC AGCGGGCAGG TTCTGCCTGC TTTGGCGGGC   3312

AGACACGCGG GCGCGATCCC ACACAGGCTG GCGGGGCCG GCCCCGAGGC CGCGTGCGTG    3372

AGAACCGCGC CGGTGTCCCC AGAGACCAGG CTGTGTCCCT CTTCTCTTCC CTGCGCCTGT   3432

GATGCTGGGC ACTTCATCTG ATCGGGGCG TAGCATCATA GTAGTTTTA CAGCTGTGTT    3492
```

```
ATCTTTGCGT GTAGCTATGG AAGTTGCATA ATTATTATTA TTATTATTAT AACAAGTGTG    3552

TCTTACGTGC CACCACGGCG TTGTACCTGT AGGACTCTCA TTCGGGATGA TTGGAATAGC    3612

TTCTGGAATT TGTTCAAGTT TTGGGTATGT TTAATCTGTT ATGTACTAGT GTTCTGTTTG    3672

TTATTGTTTT GTTAATTACA CCATAATGCT AATTTAAAGA GACTCCAAAT CTCAATGAAG    3732

CCAGCTCACA GTGCTGTGTG CCCCGGTCAC CTAGCAAGCT GCCGAACCAA AAGAATTTGC    3792

ACCCCGCTGC GGGCCCACGT GGTTGGGGCC CTGCCCTGGC AGGGTCATCC TGTGCTCGGA    3852

GGCCATCTCG GCACAGGCC CACCCCGCCC CACCCCTCCA GAACACGGCT CACGCTTACC     3912

TCAACCATCC TGGCTGCGGC GTCTGTCTGA ACCACGCGGG GGCCTTGAGG GACGCTTTGT    3972

CTGTCGTGAT GGGGCAAGGG CACAAGTCCT GGATGTTGTG TGTTCGAGAG GCCAAAGGCT    4032

GGTGGCAAGT GCACGGGCA CAGCGGAGTC TGTCCTGTGA CGCGCAAGTC TGAGGGTCTG     4092

GGCGGCGGGC GGCTGGGTCT GTGCATTTCT GGTTGCACCG CGGCGCTTCC CAGCACCAAC    4152

ATGTAACCGG CATGTTTCCA GCAGAAGACA AAAAGACAAA CATGAAAGTC TAGAAATAAA    4212

ACTGGTAAAA CCCCAAAAAA AAAAAAAAAA AA                                  4244
```

(2) INFORMATION FOR SEQ ID NO:2:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu His Gln Leu Leu Cys Cys Glu Val Glu Thr Ile Arg Arg Ala
  1               5                  10                  15

Tyr Pro Asp Ala Asn Leu Leu Asn Asp Arg Val Leu Arg Ala Met Leu
                 20                  25                  30

Lys Ala Glu Glu Thr Cys Ala Pro Ser Val Ser Tyr Phe Lys Cys Val
             35                  40                  45

Gln Lys Glu Val Leu Pro Ser Met Arg Lys Ile Val Ala Thr Trp Met
 50                  55                  60

Leu Glu Val Cys Glu Glu Gln Lys Cys Glu Glu Glu Val Phe Pro Leu
 65                  70                  75                  80

Ala Met Asn Tyr Leu Asp Arg Phe Leu Ser Leu Glu Pro Val Lys Lys
                 85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
            115                 120                 125

Asp Asn Ser Ile Arg Pro Glu Glu Leu Leu Gln Met Glu Leu Leu Leu
130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
            195                 200                 205

Val Ala Ala Val Gln Gly Leu Asn Leu Arg Ser Pro Asn Asn Phe Leu
210                 215                 220
```

```
Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
            245                 250                 255

Ser Ser Leu Arg Gln Ala Gln Gln Asn Met Asp Pro Lys Ala Ala Glu
            260                 265                 270

Glu Glu Glu Glu Glu Glu Glu Val Asp Leu Ala Cys Thr Pro Thr
            275                 280                 285

Asp Val Arg Asp Val Asp Ile
    290                 295

(2) INFORMATION FOR SEQ ID NO:3:

(i) SEQUENCE CHARACTERISTICS:
        (A) LENGTH: 150 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:3:

Met Arg Ala Ile Leu Val Asp Trp Leu Val Glu Val Gly Glu Glu Tyr
    1               5                   10                  15

Lys Leu Gln Asn Glu Thr Leu His Leu Ala Val Asn Tyr Ile Asp Arg
                20                  25                  30

Phe Leu Ser Ser Met Ser Val Leu Arg Gly Lys Leu Gln Leu Val Gly
                35                  40                  45

Thr Ala Ala Met Leu Leu Ala Ser Lys Phe Glu Glu Ile Tyr Pro Pro
        50                  55                  60

Glu Val Ala Glu Phe Val Tyr Ile Thr Asp Asp Thr Tyr Thr Lys Lys
    65                  70                  75                  80

Gln Val Leu Arg Met Glu His Leu Val Leu Lys Val Leu Thr Phe Asp
                    85                  90                  95

Leu Ala Ala Pro Thr Val Asn Gln Phe Leu Thr Gln Tyr Phe Leu His
                    100                 105                 110

Gln Gln Pro Ala Asn Cys Lys Val Glu Ser Leu Ala Met Phe Leu Gly
                115                 120                 125

Glu Leu Ser Leu Ile Asp Ala Asp Pro Tyr Leu Lys Tyr Leu Pro Ser
                130                 135                 140

Val Ile Ala Gly Ala Ala
    145             150

(2) INFORMATION FOR SEQ ID NO:4:

(i) SEQUENCE CHARACTERISTICS:
        (A) LENGTH: 152 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:4:

Met Arg Lys Ile Val Ala Thr Trp Met Leu Glu Val Cys Glu Glu Gln
    1               5                   10                  15

Lys Cys Glu Glu Glu Val Phe Pro Leu Ala Met Asn Tyr Leu Asp Arg
                20                  25                  30

Phe Leu Ser Leu Glu Pro Val Lys Lys Ser Arg Leu Gln Leu Leu Gly
```

```
              35                  40                  45
    Ala Thr Cys Met Phe Val Ala Ser Lys Met Lys Glu Thr Ile Pro Leu
                50                  55                  60

Thr Ala Glu Lys Leu Cys Ile Tyr Thr Asp Asn Ser Ile Arg Pro Glu
    65                  70                  75                  80

Glu Leu Leu Gln Met Glu Leu Leu Val Asn Lys Leu Lys Trp Asn
                    85                  90                  95

Leu Ala Ala Met Thr Pro His Asp Phe Ile Glu His Phe Leu Ser Lys
                100                 105                 110

Met Pro Glu Ala Glu Asn Lys Gln Ile Ile Arg Lys His Ala Gln
                115                 120                 125

Thr Phe Val Ala Leu Cys Ala Thr Asp Val Lys Phe Ile Ser Asn Pro
                130                 135                 140

Pro Ser Met Val Ala Ala Gly Ser
    145                 150

(2) INFORMATION FOR SEQ ID NO:5:

(i) SEQUENCE CHARACTERISTICS:
        (A) LENGTH: 149 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:5:

Met Arg Cys Ile Leu Val Asp Trp Leu Val Glu Val Ser Glu Glu Asp
    1               5                  10                  15

Lys Leu His Arg Glu Thr Leu Phe Leu Gly Val Asn Tyr Ile Asp Arg
                    20                  25                  30

Phe Leu Ser Lys Ile Ser Val Leu Arg Gly Lys Leu Gln Leu Val Gly
                35                  40                  45

Ala Ala Ser Met Phe Leu Ala Ala Lys Tyr Glu Glu Ile Tyr Pro Pro
    50                  55                  60

Asp Val Lys Glu Phe Ala Tyr Ile Thr Asp Asp Thr Tyr Thr Ser Gln
    65                  70                  75                  80

Gln Val Leu Arg Met Glu His Leu Ile Leu Lys Val Leu Thr Phe Asp
                    85                  90                  95

Val Ala Val Pro Thr Thr Asn Trp Phe Cys Glu Asp Phe Leu Lys Ser
                100                 105                 110

Cys Asp Ala Asp Asp Lys Leu Lys Ser Leu Thr Met Phe Leu Thr Glu
                115                 120                 125

Leu Thr Leu Ile Asp Met Asp Ala Tyr Leu Lys Tyr Leu Pro Ser Ile
                130                 135                 140

Thr Ala Ala Ala Ala
    145

(2) INFORMATION FOR SEQ ID NO:6:

(i) SEQUENCE CHARACTERISTICS:
        (A) LENGTH: 148 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:6:
```

```
Met Arg Ala Ile Leu Ile Asp Trp Leu Gln Val Gln Met Lys Phe
1               5                   10                  15

Arg Leu Leu Gln Glu Thr Met Tyr Met Thr Val Ser Ile Ile Asp Arg
            20                  25                  30

Phe Met Gln Asn Asn Cys Val Pro Lys Lys Met Leu Gln Leu Val Gly
            35                  40                  45

Val Thr Ala Met Phe Ile Ala Ser Lys Tyr Glu Glu Met Tyr Pro Pro
    50                  55                  60

Glu Ile Gly Asp Phe Ala Phe Val Thr Asp Asn Thr Tyr Thr Lys His
65                  70                  75                  80

Gln Ile Arg Gln Met Glu Met Lys Ile Leu Arg Ala Leu Asn Phe Gly
                85                  90                  95

Leu Gly Arg Pro Leu Pro Leu His Phe Leu Arg Arg Ala Ser Lys Ile
            100                 105                 110

Gly Glu Val Asp Val Glu Gln His Thr Leu Ala Lys Tyr Leu Met Glu
            115                 120                 125

Leu Thr Met Leu Asp Tyr Asp Met Val His Phe Pro Pro Ser Gln Ile
130                 135                 140

Ala Ala Gly Ala
145
```

(2) INFORMATION FOR SEQ ID NO:7:

(i) SEQUENCE CHARACTERISTICS:
        (A) LENGTH: 148 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:7:

```
Met Arg Gly Ile Leu Thr Asp Trp Leu Ile Glu Val His Ser Arg Phe
1               5                   10                  15

Arg Leu Leu Pro Glu Thr Leu Phe Leu Ala Val Asn Ile Ile Asp Arg
            20                  25                  30

Phe Leu Ser Leu Arg Val Cys Ser Leu Asn Lys Leu Gln Leu Val Gly
            35                  40                  45

Ile Ala Ala Leu Phe Ile Ala Ser Lys Tyr Glu Glu Val Met Cys Pro
    50                  55                  60

Ser Val Gln Asn Phe Val Tyr Met Ala Asp Gly Gly Tyr Asp Glu Glu
65                  70                  75                  80

Glu Ile Leu Gln Ala Glu Arg Tyr Ile Leu Arg Val Leu Glu Phe Asn
                85                  90                  95

Leu Ala Tyr Pro Asn Pro Met Asn Phe Leu Arg Arg Ile Ser Lys Ala
            100                 105                 110

Asp Phe Tyr Asp Ile Gln Thr Arg Thr Val Ala Lys Tyr Leu Val Glu
            115                 120                 125

Ile Gly Leu Leu Asp His Lys Leu Leu Pro Tyr Pro Pro Ser Gln Gln
130                 135                 140

Cys Ala Ala Ala
145
```

(2) INFORMATION FOR SEQ ID NO:8:

(i) SEQUENCE CHARACTERISTICS:
        (A) LENGTH: 152 amino acids
        (B) TYPE: amino acid -continued

```
      (C) STRANDEDNESS: single
      (D) TOPOLOGY: Not Relevant (ii) MOLECULE TYPE: peptide (xi) SEQUENCE DESCRIPTION: SEQ ID NO:8:

Met Arg Phe Leu Ile Phe Asp Phe Ile Met Tyr Cys His Thr Arg Leu
  1               5                   10                  15

Asn Leu Ser Thr Ser Thr Leu Phe Leu Thr Phe Thr Ile Leu Asp Lys
                  20                  25                  30

Tyr Ser Ser Arg Phe Ile Ile Lys Ser Tyr Asn Tyr Gln Leu Leu Ser
                  35                  40                  45

Leu Thr Ala Leu Trp Ile Ser Ser Lys Phe Trp Asp Ser Lys Asn Arg
              50                  55                  60

Met Ala Thr Leu Lys Val Leu Gln Asn Leu Cys Cys Asn Gln Tyr Ser
  65                  70                  75                  80

Ile Lys Gln Phe Thr Thr Met Glu Met His Leu Phe Lys Ser Leu Asp
                  85                  90                  95

Trp Ser Ile Cys Gln Ser Ala Thr Phe Asp Ser Tyr Ile Asp Ile Phe
                  100                 105                 110

Leu Phe Gln Ser Thr Ser Pro Leu Ser Pro Gly Val Val Leu Ser Ala
              115                 120                 125

Pro Leu Glu Ala Phe Ile Gln Gln Lys Leu Ala Leu Leu Asn Asn Ala
          130                 135                 140

Ala Gly Thr Ala Ile Asn Lys Ser
  145                 150
```